United States Patent
Hamblin et al.

(10) Patent No.: US 6,607,522 B1
(45) Date of Patent: Aug. 19, 2003

(54) METHODS FOR TISSUE WELDING USING LASER-ACTIVATED PROTEIN SOLDERS

(75) Inventors: Michael R. Hamblin, Revere, MA (US); John Khadem, Carlsbad, CA (US)

(73) Assignee: General Hospital Corporation, Charlestown, MA (US)

( * ) Notice: Subject to any disclaimer, the term of this patent is extended or adjusted under 35 U.S.C. 154(b) by 0 days.

(21) Appl. No.: 09/527,369

(22) Filed: Mar. 16, 2000

(51) Int. Cl.[7] .............................................. A61B 18/18
(52) U.S. Cl. ................. 606/8; 606/9; 607/88; 607/89; 128/898
(58) Field of Search .................. 607/88, 89, 96; 606/7, 8; 514/2–21; 128/898

(56) References Cited

U.S. PATENT DOCUMENTS

| | | | |
|---|---|---|---|
| 3,758,682 A | * 9/1973 | Huber et al. ............... 424/177 |
| 5,156,613 A | 10/1992 | Sawyer ....................... 60/213 |
| 5,209,776 A | 5/1993 | Bass et al. .................. 106/124 |
| 5,290,272 A | 3/1994 | Burstein et al. ............... 606/4 |
| 5,290,278 A | 3/1994 | Anderson ..................... 606/15 |
| 5,292,362 A | 3/1994 | Bass et al. .................. 106/124 |
| 5,300,065 A | 4/1994 | Anderson ..................... 606/13 |
| 5,326,616 A | 7/1994 | Butterworth et al. ........ 428/131 |
| 5,330,974 A | 7/1994 | Pines et al. .................. 514/21 |
| 5,540,677 A | 7/1996 | Sinofsky ........................ 606/8 |
| 5,552,452 A | 9/1996 | Khadem et al. ............... 522/63 |
| 5,565,551 A | 10/1996 | Lewis et al. ................. 530/405 |
| 5,569,242 A | 10/1996 | Lax et al. ...................... 606/42 |
| 5,571,216 A | 11/1996 | Anderson ..................... 623/66 |
| 5,605,887 A | 2/1997 | Pines et al. .................. 514/21 |
| 5,622,946 A | * 4/1997 | Sessler et al. ............... 514/185 |
| 5,713,891 A | 2/1998 | Poppas ........................... 606/2 |
| 5,725,522 A | * 3/1998 | Sinofsky ........................ 606/8 |
| 5,749,895 A | 5/1998 | Sawyer et al. ............... 606/214 |
| 5,766,600 A | 6/1998 | Lewis et al. ............... 424/204.1 |
| 5,824,015 A | 10/1998 | Sawyer ........................ 606/214 |
| 5,827,265 A | 10/1998 | Glinsky et al. .................. 606/8 |
| 5,846,940 A | * 12/1998 | Okamoto et al. .............. 514/17 |
| 5,854,207 A | * 12/1998 | Lee et al. ........................ 514/2 |
| 5,913,884 A | * 6/1999 | Trauner et al. ................ 607/88 |
| 5,917,045 A | 6/1999 | Lewis et al. ................. 546/100 |
| 5,925,078 A | 7/1999 | Anderson ...................... 623/66 |
| 6,015,474 A | 1/2000 | Stedronsky .................. 156/314 |
| 6,087,552 A | 7/2000 | Gregory ........................ 606/11 |
| 6,107,466 A | * 8/2000 | Hasan et al. ................. 530/351 |

OTHER PUBLICATIONS

Ashton et al., "Laser–assisted fibrinogen bonding of vascular tissue," *J. Surg. Res.*, 51:324–328, 1991.

Back et al., "Nd:YAG laser–welded canine arteriovenous anastomoses," *Lasers Surg Med.* 14:111–117, 1994.

Bailes et al., "Review of tissue welding applications in neurosurgery," *Microsurgery*, 8:242–244, 1987.

Bass and Treat, "Laser tissue welding: a comprehensive review of current and future clinical applications," *Lasers Surg. Med.*, 17:315–349, 1995.

(List continued on next page.)

*Primary Examiner*—Linda C. M. Dvorak
*Assistant Examiner*—Ahmed M Farah
(74) *Attorney, Agent, or Firm*—Fulbright & Jaworski L.L.P.

(57) ABSTRACT

Various tissue glues have drawback such as toxicity, causing inflammatory reactions or insufficient bonding strength. The invention is directed to methods of form tissue adhesion by administering to tissues compositions comprising proteins conjugated to one or more novel photosensitizers and irradiating the composition. The composition may further comprise one or more proteins not conjugated to the photosensitizer. Additionally, the present invention relates to compositions and methods wherein increased ratios of protein to photosensitizer enhance weld strength.

46 Claims, 3 Drawing Sheets

OTHER PUBLICATIONS

Basu et al., "Comparative study of biological glues: cryoprecipitate glue, two-component fibrin sealant, and "French" glue," *Ann Thorac Surg.*, 60:1255–1262, 1995.

Cheng et al., "Characterization of a fibrin glue–GDNF slow–release preparation," Cell Transplant, 7:53–61, 1998.

Dubbelman et al., "Photodynamic effects of protoporphyrin on human erythrocytes. Nature of the cross–linking of membrane proteins," *Biochem Biophys Acta.*, 511:141–151, 1978.

Eaton et al., "Sutureless cataract incision closure using laser activated tissue glues," *Proc. S.P.I.E.*, 1423:52–57, 1991.

Ennker et al., "Formaldehyde–free collagen glue in experimental lung gluing," *Ann Thorac Surg.* 57:1622–1627, 1994.

Fickweiler et al., "Indocyanine green: intracellular uptake and phototherapeutic effects in vitro," *J Photochem Photobiol B.*, 38:178–183, 1997.

Forman et al., "Laser–assisted fibrin clot soldering of human menisci," *Clin Orthop.*, 310:37–41, 1995.

Fawcett et al., "Dopaminergic neuronal survival and the effects of bFGF in explant, three–dimensional and monolayer cultures of dembryonic rat ventral mescencephalon," *Exp. Brain Res.*, 106:275–282, 1995.

Gailitis et al., "Laser welding of synthetic epikeratoplasty lenticules to the cornea," *Refract. Corneal Surg.* 6:430–436, 1990.

Goins et al., "Photodynamic biologic tissue glue to enhance corneal wound healing after radial keratotomy" *J Cataract Refract Surg.*, 23:1331–1338, 1997.

He et al., "Transplantation of cultured human retinal pgiment epithelium into rabbit subretina," *Graefes Arch. Clin. Exp. Opthalmol.*, 231:737–742, 1993.

Khadem et al., "Photodynamic biologic tissue glue,", *Cornea*, 13:406–410, 1994.

Khadem et al., "Photodynamic tissue adhesion with chlorin(e6) protein conjugates," *Invest Ophthalmol Vis Sci.*, 40:3132–3137, 1999.

Khouri et al., "Tissue generation with growth factors," Surgery, 114, 374–379, 1993.

Kim et al., "Evaluation of tissue adhesives in closure of scleral tunnel incisions," *J Cataract Refract Surg.*, 21:320–325, 1995.

Kirsch et al., "Effects of diode laser welding with dye–enhanced glue on tensile strength of sutures commonly used in urology," *Lasers Surg. Med.*, 18:167–170, 1996.

Kleinman et al., "Role of collagenous matrices in the adhesion and growth of cells," *J. Cell Biol.*, 88:473–485, 1998.

Koller and Papoutsakis, "Cell adhesion in animal cell culture; physiological and fluid mechancial implications," *Bioprocessing Technol.*, 20:61–110, 1995.

Kostenich et al., "Experimental grounds for using chlorin e6 in the photodynamic therapy of malignant tumors," *J Photochem Photobiol B.*, 22:211–217, 1994.

Lagoutte et al., "A fibrin sealant for perforated and preperforated corneal ulcers," *Br J Ophthalmol.*, 73:757–761, 1989.

Menovsky et al., "Laser(–assisted) nerve repair: a review," *Neurosurg. Rev.*, 18:225–235, 1995.

Ochsner, "Photophysical and photobiological processes in the photodynamic therapy of tumuours," *J. Photochem. Photobiol. B.*, 39:1–18, 1997.

Poppas et al., "Human albumin solder supplemented with TGF–beta 1 accelerates healing following laser welded wound closure," Lasers Surg Med, 19:360–368, 1996.

Schlossberg and Poppas, "Tissue welding with lasers," *Semin. Urol.*, 9:206–209, 1991.

Sheardown et al., "A semi–solid drug delivery system for epidermal growth factor in corneal epithelial wound healing," *Curr Eye Res*, 16:183–190, 1997.

Siedentop et al., "Autologous fibrin tissue adhesive: factors influencing bonding power," *Laryngoscope*, 98:731–733, 1988.

Sierra, "Fibrin sealant adhesive systems: a review of their chemistry, material properties and clinical applications," *J. Biomater. Appl.*, 7:309–352, 1993.

Silva and Godoy, "Riboflavin sensitized photooxidation of tyrosine," *Int J Vitam Nutr Res.*, 64:253–256, 1994.

Small et al., "Investigation of laser tissue welding dynamics via experiment and modeling," *J. Clin. Laser Med. Surg.*, 15(1):3–7, 1997.

Soukos et al., "The effect of charge on cellular uptake and phototoxicity of polylsine chlorin(e6) conjugates," *Photochem. Photobiol.*, 65:723–729, 1997.

Verweij et al., "J. Photodynamic protein cross–linking," *Biochim Biophys Acta.*, 647:87–94, 1981.

Wang, "Basic fibroblast growth factor for stimulation of bone formation in osteoinductive or conductive implants," *Acta Orthop Scand Suppl*, 269:1–33, 1996.

Williamson et al., "Biodegradable polymer film as a source of adhesion and formation of human fetal retinal pigment epithelium spheroids," *At: Assoc. of Res. in Vision and Opthalmol.*, 39:100 (Abstract 472), 1998.

Wright and Poppas, "Effect of laser wavelength and protein solder concentratino on acute tissue repair using laser welding: initial results in a canine ureter model," *Tech. Urol.*, 3:176–181, 1997.

Yamamoto et al,. "Bone regeneration by transforming growth factor beta1 released from a biodegradable hydrogel [In Process Citation]," *J Controlled Release*, 64: 133–142, 2000.

Yoshimura et al., "Photocoagulated human retinal pigment epithelial cells produce an inhibitor of vascular endothelial cell proliferation," *Invest. Ophthalmol. Vis. Sci.*, 36:1686–1691, 1995.

Zalta and Wieder, "Closure of leaking filtering blebs with cyanoacrylate tissue adhesive," *Br. J. Ophthalmol.*, 75:170–173, 1991.

Zhang and Xu, "Mechanism of photosensitized oxidation of tyrosine by gallium or zinc phthalocyanine in homogeneous and aqueous micellar media," *J Photochem Photobiol B.*, 24:109–116, 1994.

Zhang et al., "Inhibitory effects of fluorescein isothiocyanate photoactivation on lymphatic pump activity," *Microvasc Res.* 54:99–107, 1997.

Company abstract, Tissuemed Limited from the MDI conference website: http://www.medicaldata.com/conferences/emtwest99/profiles.htm, May 15, 2000.

Company profile, Tissuemed Limited, Apr. 14, 2000.

* cited by examiner

METHODS FOR TISSUE WELDING USING LASER-ACTIVATED PROTEIN SOLDERS

BACKGROUND OF THE INVENTION

1. Field of the Invention

The present invention relates generally to the fields of medical glues and adhesives. More particularly, it concerns methods and compositions for sealing of wounds and incisions. In certain aspects, the invention concerns adhesion of two or more tissue samples using proteinaceous, and/or lipoproteinaceous compositions conjugated and/or mixed with a photosensitizer or dye upon irradiation.

2. Description of Related Art

Healing and sealing tissue wounds remains a problem in medical practice. To enhance tissue healing, much effort has gone towards producing a biocompatible slow release formulation which can be introduced into a tissue defect and that will release biologically active growth factor at a steady rate for the required time. These formulations were designed to promote tissue growth or healing. Examples of these vehicles include biodegradable gelatin hydrogel (Yamamoto et al., 2000), hyaluronan (Mohammad et al., 2000), fibrin glue (Cheng et al., 1998), fibrin derivatives (Sakiyama-Elbert & Hubbell, 2000), alginate microspheres (Nehra et al., 1999), carbopol gel (Sheardown et al., 1997), derivatized dextrans (Tardieu et al., 1992), calcium alginate beads (Downs et al., 1992). It should be noted that many of these slow release vehicles do not actually bind to the tissue, they merely "sit" in the defect and slowly biodegrade. However, a TGF-beta 1 and indocyanine green albumin solder have been used in incisions in pig skin (Poppas et al., 1996). A significant increase in wound healing strength was found using TGF-beta containing solder compared to solder alone.

To replace or promote healing in damaged tissue, various forms of tissue transplants have been conducted. However, cell transplantation often requires that that the donor cells retain their polarity and function, avoid formation of clumps or multilayers, and maintain their viability. In certain tissues, a biodegradable matrix has been used to transplant cells. Three-dimensional cell culture systems with various attachment substrates offer new probabilities for long-term viability and donor cell functions (Wintermantel et al., 1992; Fawcett et al., 1995; Spier and Maroudas, 1991; Peshwa et al., 1996; Rezai et al., 1997; Ruoslahti and Hayman, 1992; Spector et al., 1993; Hoffman, 1994; Kleinman et al., 1998). Successful use of 3-dimensional micro-carriers for transplantation to the liver (Wintermantel et al., 1992) and brain (Fawcett et al., 1995) has been reported by several investigators. In 3-dimensional micro-carriers, the cultured cells are distributed at the outer surfaces and within the body of the particles (Spier and Maroudas, 1991). In a 3-dimensional carrier, more cell contacts are generated compared with a monolayer state, thereby facilitating cell proliferation and spreading (Peshwa et al., 1996; Rezai et al., 1997). The chemistry of the extracellular matrix itself can also modulate various aspects of cell behavior, including adhesion, proliferation, and migration (Ruoslahti and Hayman, 1992).

Successful retinal pigment epithelium (RPE) transplantation requires cell attachment to a substrate prevents RPE apoptosis and de-differentiation after transplantation (Tezel and Del Priore, 1997; Ho et al., 1996). Subretinal provision of RPE cells has been carried out in the form of a cell suspension, RPE patches, or RPE cells grown on artificial substrates (Li and turner, 1991; Sheedlo et al., 1989; Gabrielian et al., 1999; Bhatt et al., 1994). Cell suspension provision has the limitations of reflux from the iatrogenic retinotomy site and irregular distribution of the donor cells in the subretinal space (Wongpichedchai et al., 1992). Retinal pigment epithelium patch grafts, although probably the most physiologic, have not been shown to proliferate in vivo (Gouras et al., 1994; Berglin et al., 1997).

Sealing tissue wounds usually involves sutures and other mechanical seals. Alternative methods to the traditional mechanical means of closing incisions, wounds, and anastomoses have received attention. These may be divided into three groups: first, biological glues (Basu et al., 1995) such as fibrin sealant (Sierra, 1993) and gelatin-resorcinol glue (Albes et al., 1993); second, a technique known as laser tissue welding, which relies on carbon dioxide (Rooke et al., 1993) or Nd:YAG (Back et al., 1994) lasers to produce thermal effects to attach tissue surfaces; and third, chromophore-assisted laser welding (Bass and Treat, 1995) using protein solders that contain a light-absorbing dye together with a laser that emits the appropriate wavelength light. This pairing is most commonly that of fluorescein and a 532-nm frequency-doubled Nd:YAG laser, or indocyanine green and an 805-nm diode laser (Wright and Poppas, 1997).

Alternative tissue adhesives have drawbacks. Cyanoacrylate glues, which have been most frequently used in ophthalmology (Leahey et al., 1993) can be toxic, causing inflammatory reactions and are nonbiodegradable (Siegal and Zaidman, 1989). Fibrin sealants (Spontnitz, 1995) are not particularly effective, form bonds of insufficient strength (Basu et al., 1995; Siedentop et al., 1988), present the possibility of viral infection if prepared from pooled human plasma, and may inhibit would healing (van der Ham et al., 1993). Resorcinol gelatin sealants (Albes et al., 1993) can damage tissue because they contain formaldehyde (Ennker et al., 1994). However, laser-activated tissue solders allows safe preparation and sterilization of the material, because it is activated only under laser illumination and is thought unlikely to lead to tissue toxicity (Bass and Treat, 1995).

Laser tissue welding have been used in urology (Kirsch et al., 1997), vascular surgery (Ashton et al., 1991), neurosurgery (Menovsky et al., 1995), and orthopedics (Forman et al., 1995). Ophthalmologic applications of laser welding with chromophore-assisted protein solder have included sealing cataract incisions (Eaton et al., 1991) and scleral tunnel incisions (Kim et al., 1995) and bonding synthetic epikeratoplasty lenticules to the cornea (Gailitis et al., 1990).

Laser tissue welding without added dye must proceed through a purely thermal mechanism (Schober et al., 1986), whereby the edges of the collagen are partially "unraveled" and can then recombine to form noncovalent bonds (Pearce and Thomsen, 1993). It was thought that dye-assisted welding with protein solders also proceeded through a thermal mechanism, with the chromophore-absorbing energy, releasing it as heat, denaturing the protein in the solder and forming noncovalent bonds between the added protein solder and the tissue collagen (Small et al., 1997). A mixture of cryoprecipitated fibrinogen and a dye that absorbs laser energy and releases it in the form of heat at the wound interface has been used in tissue adhesion (Moazami, et al., 1990; Oz et al., 1990).

However, results with the two dyes most commonly used for tissue welding, fluorescein and indocyanine green, have produced evidence that photochemical processes occur as well. It has been reported that fluoresceindextran in the rat mesentery lymphatics when illuminated produce changes that could be attributed to singlet oxygen (Zhang et al., 1997). Studies with indocyanine green in vitro have shown that it has a triplet yield of 0.11, and singlet oxygen can be detected by time-resolved luminescence techniques (Baumier et al., 1997; Fickweller et al., 1997). Laser welding with a biologic tissue glue consisting of 18% fibrinogen with 2.6 mg/ml r-5-P showed reduction of the weld strength in the presence of azide which is evidence of singlet oxygen involvement in the weld formation (Khadem et al., 1994).

These chemicals that cause photo-oxidative effects when exposed to visible light have been called "photosensitizers" (Chacon et al., 1988; Tanielian C., 1986; Foote, C. S., 1976). There are two main classes of photosensitizer: tetrapyrroles including porphyrins, chlorins, bacteriochlorins, phthalocyanines, naphthalocyanines, texaphyrins, verdins, purpurins; pheophorbides, etc; and non-tetrapyrrole dyes, including flavins, xanthenes, thiazines, selenium and tellurium analogues of thiazines, azines, triarylmethanes, etc. Fluorescein is a xanthene but is not considered a photosensitizer because it releases absorbed energy primarily in the form of heat and fluorescence. Some of these dyes have been evaluated with proteins as tissue glues with varying success (U.S. Pat. No. 5,552,452).

Chlorin$_{e6}$ (C$_{e6}$) has been investigated as a photosensitizer for photodynamic therapy both as the free dye (Kostenich et al., 1994) and conjugated to proteins, (Schmidt-Erfurth et al., 1997), macromolecules (Soukos et al., 1997) and particles (Bachor et al., 1991). Covalent conjugates between C$_{e6}$ and monoclonal antibodies (Hamblin et al., 1996) and poly-$_L$-amino acids (Soukos et al., 1997) for the photodynamic therapy of cancer have been described. C$_{e6}$ is usually thought to act as a photosensitizer by transferring energy from the triplet state to the ground state of molecular oxygen, producing the exited singlet oxygen molecule, a process known as type II photosensitization (Ochsner, 1997). Singlet oxygen can then react with certain amino acids in proteins, particularly histidine, tryptophan, tyrosine, cysteine, and methionine (Dubbelman et al., 1978). One mechanism that has been elucidated for the formation of intermolecular protein cross-links is the reaction of oxidized histidine with free amino groups of lysines on neighboring proteins (Verweij et al., 1981), but it is recognized that other mechanisms must operate as well. There is another possible photo-oxidation pathway involving electron transfer from the photosensitizer triplet state producing either a radical cation or a radical anion, which is known as type I photosensitization (Zhang and Xu, 1994). These radical ions can then react further with oxygen producing carbon and oxygen centered radicals and superoxide anions (Laustrait, 1986). A mechanism for the radical mediated cross-linking of proteins involves the formation of dityrosine (Gill et al., 1997) by phenolic coupling of tyrosine residues on neighboring chains.

Despite these advances in the understanding of tissue healing, tissue transplantation and tissue welding mechanisms, their exists a need for improved methods to heal, transplant and/or weld tissue. Improved methods to promote tissue healing or aid in successful tissue transplants would provide significant benefits in the art. Tissue welds with improved strength would resist tearing under stress. Additionally, there exists a need for methods and compositions of tissue welding, wound healing and tissue transplantation that are easy to handle during surgery, and possess a reduced toxicity or scaring potential.

SUMMARY OF THE INVENTION

The present invention overcomes the deficiencies of the prior art by providing novel compositions and methods for tissue welding. The invention also provides compositions and methods for administering an active agent to a tissue. Such active agents may be living cells. Thus, in certain embodiments, the invention provides a method to transplant tissue. Such transplanted cells may be formed into a desired shape, such as a monolayer.

The invention first provides a method to weld tissue together, comprising the steps of: applying to at least one tissue a composition comprising at least one photosensitizer and at least one proteinaceous compound or at least one lipid; and irradiating the composition with electromagnetic energy; wherein the irradiating promotes adhesion of the tissue to at least a second tissue. In certain embodiments, the photosensitizer is a cationic azine mon-azo dye or derivative thereof. In certain aspects, the cationic azine mono-azo dye is neutral red or Janus Green. In other embodiments, the photosensitizer is a tri-arylmethane dye or derivative thereof. In particular aspects, the tri-arylmethane dye is Malachite Green, Brilliant Green, Crystal Violet, basic fuschin, pararosaniline acetate, methyl green or new fuschin. In certain aspects, the tri-arylmethane dye is a zwitterionic triarylmethane dye, such as patent blue VF. In other embodiments, the photosensitizer is a tetrapyrrole or a derivative thereof. In certain aspects, the tetrapyrrole is a porphyrin, chlorin, bacteriochlorin, phthalocyanine, naphthalocyanine, texaphyrin, verdin, purpurin or pheophorbide. In some aspects, the chlorin is chlorin$_e$6. In other aspects, the phthalocyanine is a Zn(II)-phthalocyanine, an aluminum sulfonated and disulfonated phthalocyanine or a phthalocyanine without a metal substituent. In certain aspects, the naphthalocyanine is a sulfonated aluminum naphthalocyanine. In other aspects, the pheophorbide is a pyropheophorbide. In certain embodiments, the photosensitizer is a cationic thiazine dye or derivative thereof. In particular embodiments, the cationic thiazine dye is Azure A, Azure B, Azure C, Brilliant Green, Crystal Violet or Patent Blue VF.

In certain embodiments, the composition further comprises at least a second photosensitizer. In particular aspects, the at least a second photosensitizer is a cationic azine mon-azo dye, a tri-arylmethane dye, a tetrapyrrole, a cationic thiazine dye, xanthine, an anthracenedione, an anthrapyrazole, an aminoanthraquinone, a phenoxazine dye, a phenothiazine derivative, a chalcogenapyrylium dye or derivatives thereof.

In certain embodiments, the composition comprises at least one proteinaceous compound. In certain aspects, the proteinaceous compound comprises at least one peptide, polypeptide or protein. In particular aspects, the protein is albumin, fibrinogen or gelatin.

In some embodiments, the composition is a non-covalent mixture. In other embodiments, at least one covalent bond conjugates the photosensitizer to the proteinaceous material or the lipid. In particular aspects, the covalent bond is part of a linking moeity.

In other embodiments, the composition comprises at least a second proteinaceous compound not covalently conjugated to the photosensitizer. In certain aspects, the proteinaceous compound covalently conjugated to the photosensitizer is the same type as the proteinaceous compound not covalently conjugated to the photosensitizer, such as albumin for both proteinaceous compounds.

In certain embodiments, the ratio of total proteinaceous molecules in the composition and the at least one photosensitizer is from about 100:1 to about 1:100. In certain aspects, the ratio of total proteinaceous molecules in the composition and the at least one photosensitizer is from about 10:1 to about 1:10. In other aspects, the ratio of total proteinaceous molecules in the composition and the at least one photosensitizer is from about 3:1 to about 1:1. In a particular aspect, the ratio of total proteinaceous molecules in the composition and the at least one photosensitizer is about 2:1.

In some embodiments, the composition comprises at least one lipid. In certain aspects, the lipid further comprises at least one proteinaceous compound. In other aspects, the proteinaceous compound is a lipoprotein.

In certain embodiments, the composition further comprises at least one therapeutic agent. In particular aspects, the agent is a chemical, a drug, a proteinaceous molecule, a nucleic acid, a lipid, an antibody, an antigen, a hormone, a nutritional substance, a cell or a combination thereof In certain aspects, the hormone is a growth factor, including but not limited to transforming growth factor beta, basic fibroblast growth factor, epidermal growth factor, vascular endothelial growth factor, nerve growth factor, acidic fibroblast growth factor, insulin like growth factor, heparin binding growth factor, brain-derived neurotrophic factor, glial cell line-derived neurotrophic factor, platelet-derived growth factor, leukemia inhibitory factor or combination thereof. In other aspects, the agent is a cell, including but not limited to an embryonic cell.

In other embodiments, the tissue is skin, bone, neuron, axon, cartilage, blood vessel or cornea. In certain aspects, the second tissue is the same tissue type as the at least a first tissue, while in other aspects, the second tissue is a different tissue type as the at least one tissue.

In certain embodiments, the composition is applied at of from about 10 mg the composition per $cm^2$ of the tissue to about 500 mg the composition per $cm^2$ of the tissue. In particular aspects, the composition is applied of from about 20 mg the composition per $cm^2$ of the tissue to about 100 mg the composition per $cm^2$ of the tissue.

In particular embodiments, the composition has a viscosity of about 40 to about 100 poise before the irradiation.

The invention next provides a method to weld tissue together, comprising the steps of: applying to at least one tissue a composition comprising at least one photosensitizer; and irradiating the composition with electromagnetic energy; wherein the photosensitizer is a cationic azine mon-azo dye, a tri-arylmethane dye, a chlorine, a tetrapyrrole, a cationic thiazine dye, or derivatives thereof; and wherein the irradiating promotes adhesion of the tissue to at least a second tissue. In certain embodiments, the photosensitizer is neutral red, Janus Green, Malachite Green, Brilliant Green, Crystal Violet, basic fuschin, pararosaniline acetate, methyl green, new fuschin, patent blue VF12, chlorin$_e$6, Azure A, Azure B, Azure C, Brilliant Green, Crystal Violet or Patent Blue VF. In particular aspects, the photosensitizer is Janus Green, Malachite Green or chlorin$_e$6.

In certain embodiments, the composition further comprises at least a second photosensitizer. In particular aspects, the at least a second photosensitizer is a cationic azine mon-azo dye, a tri-arylmethane dye, a tetrapyrrole, a cationic thiazine dye, xanthine, an anthracenedione, an anthrapyrazole, an aminoanthraquinone, a phenoxazine dye, a phenothiazine derivative, a chalcogenapyrylium dye or derivatives thereof.

In other embodiments, the composition comprises at least one proteinaceous compound or lipid.

In certain embodiments, the method of claim 56, wherein the composition is a non-covalent mixture. In some embodiments, the at least one covalent bond conjugates the photosensitizer to the proteinaceous material or the lipid. In particular aspects, the covalent bond is part of a linking moeity.

In some embodiments, the composition comprises at least a second proteinaceous compound not covalently conjugated to the photosensitizer. In certain aspects, the proteinaceous-compound covalently conjugated to the photosensitizer is the same type as the proteinaceous compound not covalently conjugated to the photosensitizer.

In particular embodiments, the composition further comprises at least one therapeutic agent. In some aspects, the agent is a chemical, a drug, a proteinaceous molecule, a nucleic acid, a lipid, an antibody, an antigen, a hormone, a nutritional substance, a cell or a combination thereof.

The invention further provides a method to deliver a therapeutic agent to at least one living cell, comprising the steps of: applying to at least one cell a composition comprising at least one at least one photosensitizer and at least a therapeutic agent; and irradiating the composition with electromagnetic energy; wherein the irradiating promotes adhesion of the composition to the cell, and wherein the agent is thereby contacted with the cell. In certain aspects, the photosensitizer is a cationic azine mon-azo dye, a tri-arylmethane dye, a chlorine, a tetrapyrrole, a cationic thiazine dye, or derivatives thereof. In other aspects, the photosensitizer is neutral red, Janus Green, Malachite Green, Brilliant Green, Crystal Violet, basic fuschin, pararosaniline acetate, methyl green, new fuschin, patent blue VF12, chlorin$_e$6, Azure A, Azure B, Azure C, Brilliant Green, Crystal Violet or Patent Blue VF. In particular aspects, the photosensitizer is Janus Green, Malachite Green or chlorin$_e$6.

In certain embodiments, the composition further comprises at least a second photosensitizer. In some aspects, the at least a second photosensitizer is a cationic azine mon-azo dye, a tri-arylmethane dye, a tetrapyrrole, a cationic thiazine dye, xanthine, an anthracenedione, an anthrapyrazole, an aminoanthraquinone, a phenoxazine dye, a phenothiazine derivative, a chalcogenapyrylium dye or derivatives thereof.

In particular embodiments, the composition comprises at least one proteinaceous compound or lipid.

In other embodiments, the composition is a non-covalent mixture. In some embodiments, at least one covalent bond conjugates the photosensitizer to the proteinaceous material or the lipid. In particular aspects, the covalent bond is part of a linking moeity. In certain aspects, the composition comprises at least a second proteinaceous compound not covalently conjugated to the photosensitizer. In other aspects, the proteinaceous compound covalently conjugated to the photosensitizer is the same type as the proteinaceous compound not covalently conjugated to the photosensitizer.

In some embodiments, the agent is a chemical, a drug, a proteinaceous molecule, a nucleic acid, a lipid, an antibody, an antigen, a hormone, a nutritional substance, a cell or a combination thereof. In particular aspects, the hormone is a growth factor. In other aspects, the growth factor is transforming growth facto beta, basic fibroblast growth factor, epidermal growth factor, vascular endothelial growth factor, nerve growth factor, acidic fibroblast growth factor, insulin like growth factor, heparin binding growth factor, brain-derived neurotrophic factor, glial cell line-derived neurotrophic factor, platelet-derived growth factor, leukemia inhibitory factor or combination thereof. In other aspects, the agent is a cell. In specific aspects, the cell is an embryonic cell.

In certain embodiments, a tissue may comprise, but is not limited to, skin, bone, neuron, axon, cartilage, blood vessel, cornea, muscle, facia, brain, prostate, breast, endometrium, lung, pancreas, small intestine, blood, liver, testes, ovaries, cervix, colon, skin, stomach, esophagus, spleen, lymph node, bone marrow, kidney, peripheral blood, embryonic or ascite tissue, and all cancers thereof. In certain embodiments, a cell may comprise, but is not limited to, skin, bone, neuron, axon, cartilage, blood vessel, cornea, muscle, facia, brain, prostate, breast, endometrium, lung, pancreas, small intestine, blood, liver, testes, ovaries, cervix, colon, skin, stomach, esophagus, spleen, lymph node, bone marrow, kidney, peripheral blood, embryonic or ascite cell, and all cancers thereof.

The invention additionally provides a tissue glue/biomatrix composition, comprising at least one photosensitizer and at least one proteinaceous compound or at least one lipid. In certain embodiments, the photosensitizer is a cationic azine mon-azo dye, a tri-arylmethane dye, a chlorine, a tetrapyrrole, a cationic thiazine dye, or derivatives thereof. In other embodiments, the photosensitizer is neutral red, Janus Green, Malachite Green, Brilliant Green, Crystal Violet, basic fuschin, pararosaniline acetate, methyl green, new fuschin, patent blue VF12, $chlorin_e6$, Azure A, Azure B, Azure C, Brilliant Green, Crystal Violet or Patent Blue VF. In particular aspects, the photosensitizer is Janus Green, Malachite Green or $chlorin_e6$. In other embodiments, the composition further comprises a therapeutic agent. In certain aspects, the agent is a chemical, a drug, a proteinaceous molecule, a nucleic acid, a lipid, an antibody, an antigen, a hormone, a nutritional substance, a cell or a combination thereof.

The invention next provides a tissue glue/biomatrix composition, comprising at least one photosensitizer, wherein the photosensitizer is a cationic azine mon-azo dye, a tri-arylmethane dye, a chlorine, a tetrapyrrole, a cationic thiazine dye, or derivatives thereof. In certain embodiments, the composition further comprises at least one therapeutic agent, a proteinaceous compound or lipid.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Following long-standing patent law convention, the word "a" and "an" mean "one or more" in this specification, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
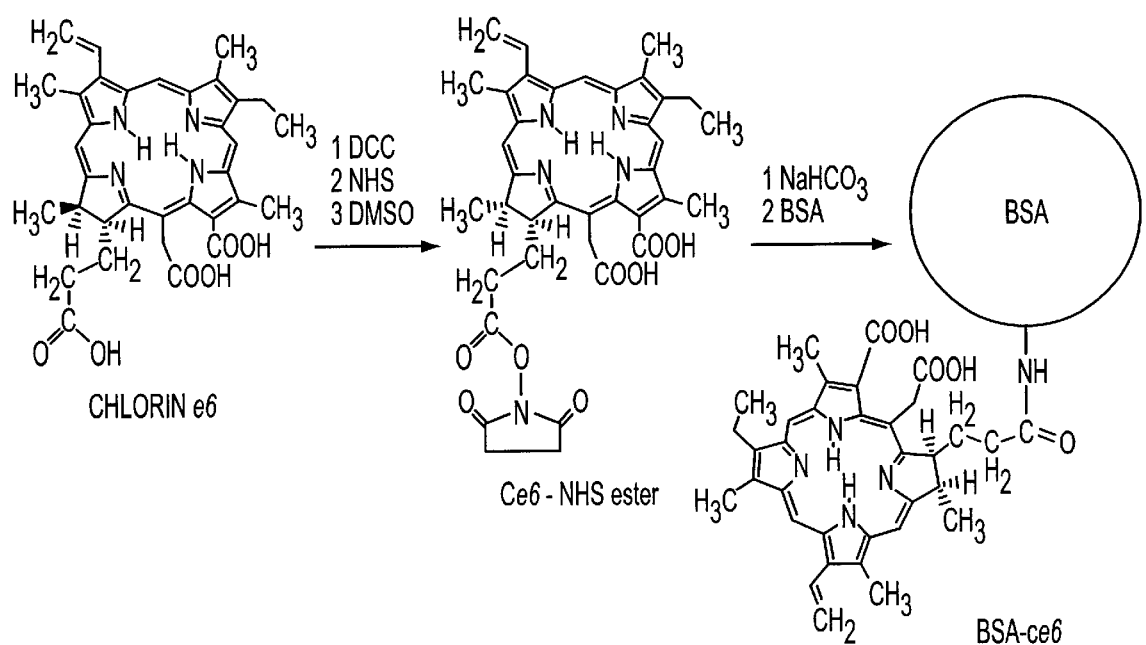
FIG. 1. Reaction scheme used to prepare covalent protein $C_{e6}$ conjugates. DCC, dicyclohexylcarbodiimide; NHS, N-hydroxysuccinimide, DMSO, dimethyl sulfoxide.

Tissue welding with the aid of laser or light-activated solders would allow sutureless surgery, as well as repair of certain wounds that are difficult or impossible to close by standard suture techniques. This is useful in the field of ophthalmology, because sutures, staples, and clips all involve additional tissue injury, and a foreign body response that can lead to increased inflammation, scarring and stenosis. In addition, gluing or welding tissue may reduce wound slippage and render the wound impermeable to microorganisms. The ideal material to use as a glue or solder should be strong, effective, nontoxic, biodegradable and available in a sterile preparation. For the solder preparation to be effective, it should also have a sufficiently high viscosity to enable it to stay in contact with the wound during welding. The composition may be applied by any method described herein or would be know to one of ordinary skill in the art, including but not limited to delivery through a convenient devise such as a needle. The ideal consistency would therefore be thixotropic (i.e., a material that has lower viscosity at higher shear stresses). There are many potential applications of this technology in ophthalmology including the repair of leaking filtering blebs (Zalta and Wieder, 1991), corneal ulcers (Golubovic and Parunovic, 1991), and scleromalacia perforans (Enzenauer et al., 1992). It may be used in construction of a temporary tarsorrhaphy (Donnenfeld et al., 1991), and the reinforcement of sclera in patients with thin sclera (Sternberg et al., 1988) or staphyloma (Coroneo et al., 1988).

To provide improved methods and compositions for laser mediated tissue welding, various compositions of dyes and proteins conjugated together were examined. Tissue glue covalent bond formation mediated by a photodynamic process were compared in a protein solder comprising protein and $C_{e6}$ covalent conjugates to noncovalent mixtures comprising protein and $C_{e6}$. The inventors reasoned that a photosensitizer molecule already joined to the protein would be more likely to form a bond between that protein and a neighboring protein molecule than a photosensitizer that had to be close to two protein molecules at the same time. The finding that the strength of the weld formed by the bovine serum albumin-$Chlorin_{e6}$ (BSA-$C_{e6}$) conjugate was significantly stronger than that formed by the noncovalent mixture was demonstrated. Additionally, it was also demonstrated that a photosensitizer widely thought to proceed through a type II photosensitization mechanism could form satisfactory tissue welds when applied in protein solder.

In particular, a photosensitizer which has known triplet and singlet oxygen quantum yields, namely $C_{e6}$, was examined for its tissue weld enhancing properties. A surprising and drastic improvement in weld strength when the protein-to-$C_{e6}$ ratio is increased from about 100 molecules of protein to about 1 molecule dye to about 1 molecule protein to about 100 molecules dye was observed. This enhancement in weld strength may be due to an increased likelihood of intermolecular cross-links forming between one conjugate molecule and one unconjugated albumin molecule than between two conjugate molecules. It is contemplated that ranges of proteinaceous molecule and/or lipid molecule to dye ratios that may be useful include, but are not limited to, about 100:1 about 95:1, about 90:1, about 85:1, about 80:1, about 75:1, about 70:1, about 65:1, about 60:1, about 55:1, about 50:1, about 45:1, about 40:1, about 35:1, about 30:1, about 25:1, about 20:1, about 17:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:17, about 1:20, about 1:25, about 1:30, about 1:35, about 1:40, about 1:45, about 1:50, about 1:55, about 1:60, about 1:65, about 1:70, about 1:75, about 1:80, about 1:85, about 1:90, about 1:95, about 1:100, and all ranges derivable therein. It is contemplated that ranges of proteinaceous molecule and/or lipid molecule to dye ratios of about 3:1, about 2:1, and about 1:1 are preferable. A particularly preferred range is about 2 molecules of lipid, protein, polypeptides and/or peptides to 1 molecule of dye. In some aspects, the proteinaceous material and/or lipid and dye are not connected by a covalent bond, anid the composition comprises essentially non-covalently associated lipid, protein, polypeptide and/or peptide-dye compositions. In other aspects, some or all of the proteinaceous and/or lipid material is covalently attached to the dye. It is contemplated that about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100 percent, and any range derivable therein, of the at least one lipid, protein, polypeptide and/or peptide is covalently conjugated to the at least one dye before photoactivation. In other aspects, it is contemplated that about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100 percent, and any range derivable therein, of the at least one dye is covalently conjugated to the at least one lipid, protein, polypeptide and/or peptide before photoactivation. As used herein, "any range derivable therein" means ranges selected from the numbers described in the specification. In a non-limiting example, ranges of about 76 to about 78 percent, about 33 to about 98 percent, etc., of at least one dye may be covalently conjugated to a polypeptide in the composition before photoactivation, based on the numbers described above.

With this discovery of compositions and methods that produce greater tissue weld strength, it is now possible to provide superior tissue welds for various medical disorders. In ophthalmology, it is contemplated that the tissue welding compositions described herein may be applied to help close incision or seal leaks in tissues including but not limited to the cornea, lens, retina or ciliary body. In urology, it is contemplated the compositions and methods herein may be used to help close incisions, seal leaks or anastomoses in tissues including but not limited to a kidney capsule, urethra, ureter urinary bladder. It is also contemplated that the compositions and methods may be used in closing reproductive tissues, such as in a vasectomy. In the gastrointestinal system, it is contemplated that the methods and compositions herein may be used to help seal anastromoses in tissues including but not limited to the esophagus, small intestine or colon, as well as help seal incisions in the pericardium, and embolize unwanted vessels. It is particularly contemplated that the compositions and methods of the present invention will have applicability in endoscopic surgery. In neurology, it is contemplated that the present invention may be used in sealing leaks or incisions in dura, sealing leaks of cerebro-spinal fluid after surgery or sealing leaks of cerebral veins. In oral settings, it is contemplated that the present invention will have use in helping seal incisions in gingivae and pharyngotomies. In the respiratory system, it is contemplated that the compositions and methods described herein will have use in aiding the sealing of leaks in lungs after pneumonectomies, and sealing leaks or incisions in pleura. In dermatology, it is contemplated that the present invention will help seal incisions where sutures are contra-indicated, such as in cosmetic applications or where hypertrophic scarring is possible. Of course, one of skill in the art will recognize that there are additional applications beyond those listed above for the tissue glue or welding methods and compositions described herein, and all such uses are encompassed by the present invention.

A. Photosensitizers

The term "photosensitizer", as used herein, refers to a compound capable of undergoing photoactivation as described above. Accordingly, photosensitizers can be characterized functionally as those chemicals which absorb electromagnetic energy, such as optical energy, and convert it primarily to chemical energy. Preferred photosensitizers for use in accordance herewith will be compounds capable of causing a photo-oxidative effect, and in particular, those capable of producing singlet oxygen when exposed to light.

Photosensitizers have typically been use as cytotoxic or histotoxic agents in the presence of light. The highly reactive free radical and radical anion species produced by these agents have been shown to cause oxidative damage to human lens enzymes, (Jedziniak, 1987) and to ocular proteins of other species. This histotoxic effect has also been exploited in their use in photodynamic cancer therapies.

There are two major types of sensitized photo-oxidative process, Type I and Type II. The sensitizer in its ground state $S_0$ first absorbs light energy to form $S_1$ and $T_1$ which are sensitizer molecules in their excited singlet and triplet states, respectively. Both Type I and Type II reactions then proceed via the triplet state because it has a much longer lifetime than the singlet state.

In Type I reactions, the sensitizer triplet $T_1$ then directly binds to the substrate to produce substrate free radicals or radical anions. The substrate radicals then can undergo further reactions, including that with molecular oxygen to form the superoxide anion $O_2$. The superoxide anion then can react in numerous ways. For example, the superoxide anion can further react to generate hydrogen peroxide ($H_2O_2$) and the hydroxyl radical (OH).

In Type II reactions, the sensitizer triplet most commonly reacts first with molecular oxygen to produce singlet oxygen ($O_2$). The singlet oxygen then oxidizes the substrate to form photo-oxidation products. Direct electron transfer from triplet to oxygen also occurs to yield superoxide anions but much less efficiently.

Photosensitizers then cause oxidative damage to susceptible amino acid residues, namely histidine, tryptophan, tyrosine, cysteine, and methionine. They are known to cause non-disulfide covalent cross-links in susceptible proteins (Goosey et al., 1980; Girotti et al., 1979). This process is oxygen dependent and seems to be mediated by singlet oxygen rather than by superoxide anions, hydrogen peroxide, or hydroxyl radicals. Natural collagen is devoid of disulfide bridges (Stimler et al., 1977).

The photosensitizer element of the composition will be used in an amount effective to promote the formation of an adhesive upon photoactivation; i.e., to generate a photo-oxidative effect sufficient to form an adhesive. These terms are used to refer to the process by which the photosensitizer, when exposed to light, produces singlet oxygen in sufficient quantities to cause oxidative damage to amino acids. As used herein, the term "photoactivation" is used generally to describe the process by which energy in the form of electromagnetic radiation is absorbed by a compound which becomes "excited" and then functions to convert the energy to another form of energy, preferably chemical energy. The chemical energy will be in the form of reactive oxygen species like singlet oxygen, superoxide anion, hydroxyl radical, the excited state of the photosensitizer, photosensitizer free radical or substrate free radical species. The electromagnetic radiation will include "optical energy", i.e., will have a wavelength in the visible range or portion of the electromagnetic spectrum, and will also include the ultra violet and infra red regions of the spectrum. The photoactivation processes associated with the present invention may be those which involve reduced, negligible, or no conversion or transfer of the absorbed energy into heat energy and, hence, are associated with increased or enhanced transfer of the absorbed energy into chemical energy. The photoactivation occurs with no more than a 1–2 degree Celsius rise in temperature, preferably no more than 1° C. rise and more preferably no more than 0.5° C.

The damage, i.e., chemical modification, to the amino acids results in the formation of covalent bonds or cross-links between distinct amino acids, thus allowing the formation of a proteinaceous adhesive, seal or framework. It is the generation of this proteinaceous adhesive, using exogenous protein, polypeptide or peptide containing compositions and/or endogenous tissue components, which allows tissues to be sealed and wounds or other incisions to be closed.

This oxidative damage takes the form of the excited state of photosensitizer molecules and reactive oxygen species as well as substrate free radicals which are capable of reacting with a wide variety of compounds. The photosensitizers described herein may thus also be characterized as compounds capable of photo-oxidatively damaging or modifying the amino acids of the protein and thus causing the presence of highly reactive species and thus promoting the cross-linking reactions.

Examples of photosensitive compounds for use herewith include various light-sensitive dyes and biological molecules such as, for example, cationic azine mon-azo dyes, including but not limited to Janus Green B or neutral red; tri-arylmethane dyes, including but not limited to Malachite Green, Brilliant Green, Crystal Violet, basic fuschin, para-rosaniline acetate, methyl green or new fuschin; zwitterionic triarylmethane dyes including but not limited to patent blue VF; chlorines or tetrapyrroles, including but not limited to chlorin$_{e6}$; cationic thiazine dyes, including but not limited to Azure A, Azure B, Azure C, methylene blue or toluidine blue O; or any photosensitive derivatives thereof. As mentioned above, compounds which absorb and convert electromagnetic energy, but which release a substantial amount of heat energy and do not significantly produce reactive oxygen species, are not contemplated as preferable for use in the present invention. For example, fluorescein is a xanthene, but is not considered a photosensitizer as it releases absorbed energy primarily in the form of heat and fluorescence.

Photosensitizers include, but are not limited to, hematoporphyrins, such as hematoporphyrin HCI and hematoporphyrin esters (Dobson, J. and M. Wilson, 1992); dihematophorphyrin ester (Wilson, M. et al., 1993); hematoporphyrin IX (Russell et al., 1991, available from Porphyrin Products, Logan, Utah) and its derivatives; 3,1-mesotetrakis (o-propionamidophenyl)porphyrin; hydroporphyrins such as chlorin, herein, and bacteriochlorin of the tetra (hydroxyphenyl)porphyrin series, and synthetic diporphyrins and dichlorins; o-substituted tetraphenyl porphyrins (picket fence porphyrins); chlorin$_e$6 monoethylendiamine monamide (CMA Goff, B. A. et al., 1994, available from Porphyrin Products, Logan, Utah); mono-1-aspartyl derivative of chlorin$_e$6, and mono- and di-1-aspartyl derivatives of chlorin$_e$6; the hematoporphyrin mixture, Photofrin II (QuadraLogic Technologies, Inc., Vancouver, BC, Canada); benzoporphyrin derivatives, including benzoporphyrin derivative mono acid Ring A (BPD-MA), tetracyanoethylene adducts, dimethyl acetylene dicarboxylate adducts, Diels-Alder adducts, and monoacid ring "a" derivatives; a naphthalocyanine (Biolo, R., 1994); a Zn(II)-phthalocyanine (Shopora, M. et al., 1995); toluidine blue O (Wilson, M. et al., 1993); aluminum sulfonated and disulfonated phthalocyanine ibid.; and phthalocyanines without metal substituents, and with varying other substituents; a tetra sulfonated derivative; sulfonated aluminum naphthalocyanines; methylene blue (ibid); nile blue; crystal violet; azure β chloride; and rose bengal (Wilson, M., 1994, Intl. Dent. J. 44: 187–189). Numerous photosensitizer entities are disclosed in Wilson, M. et al., 1992, and in Okamoto, H. et al., 1992, each incorporated herein by reference. Other potential photosensitizer compositions include but are not limited to, pheophorbides such as pyropheophorbide compounds, anthracenediones; anthrapyrazoles; aminoanthraquinone; phenoxazine dyes; phenothiazine derivatives; chalcogenapyrylium dyes including cationic selena- and tellurapyrylium derivatives; verdins; purpurins including tin and zinc derivatives of octaethylpurpurin and etiopurpurin; benzonaphthoporphyrazines; cationic imminium salts; and tetracyclines. Particularly preferred photosensitizers are Chlorin$_e$6, Janus Green, Malachite green or Phthalocyanines. It is contemplated that the compositions disclosed herein may further comprise any combination of photosensitizers disclosed herein or know to one of skill in the art, and may be used in the methods of the present invention.

The choice of one or more photosensitizers will generally be made in conjunction with the choice of electromagnetic radiation contemplated for use in exciting the compound, as will be understood by those of skill in the art in light of the present disclosure.

In preferred embodiments, it is contemplated that one would wish to employ a substantially water-soluble photosensitizer, particularly where the photosensitizer, or combined composition, is intended for use in connection with a substantially aqueous tissue environment such as, e.g., the eye. However, water-solubility is only required to the extent that the photosensitizer is able to form a substantially soluble composition on contact with either the lipid, protein, polypeptide and/or peptide containing composition, the tissue itself, or a combination of the two. In certain embodiments, the photosensitizer may be lipophilic, and its solubility is enhanced by the presence of amphipathic proteinaceous and/or lipid materials or constructs, or other materials that may aid solubility (i.e., emulsify the photosensitizer). "Substantially soluble" indicates that the various components of the composition and tissue are able to functionally interact and that there is no significant particulate matter formed which may cause or contribute to an adverse biological reaction.

B. Proteinaceous Compositions

In certain embodiments, the present invention concerns novel compositions comprising a proteinaceous composition conjugated with at least one photosensitizer. As used herein, a "proteinaceous composition", "proteinaceous compound" or "proteinaceous material" refers to a protein of greater than about 200 amino acids or the full length endogenous sequence translated from a gene, a polypeptide of greater than about 100 amino acids, and/or a peptide of from about 3 to about 100 amino acids. In certain embodiments the size of the at least one protein, polypeptide or peptide chain may be, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater residues in length, and any range derivable therein.

The term "proteinaceous composition" encompasses sequences comprising at least one of the 20 common amino acids in naturally synthesized proteins, or at least one modified or unusual amino acid, including but not limited to those shown on Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In certain embodiments the proteinaceous composition comprises at least one protein, polypeptide or peptide. In further embodiments the proteinaceous composition comprises a biocompatible protein, polypeptide or peptide. As used herein, the term "biocompatible" refers to a substance which produces no significant untoward effects when applied to, or administered to, a given animal or human subject according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

In certain embodiments, the proteinaceous composition may comprise at least one antibody. It is contemplated that antibodies to specific tissues may bind the tissue(s) and foster tighter adhesion of the glue to the tissues after welding. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

It is contemplated that virtually any protein, polypeptide or peptide containing component may be used in the compositions and methods disclosed herein. However, it is preferred that the proteinaceous material is biocompatible. In certain embodiments, it is envisioned that the formation of a more viscous composition will be advantageous in that will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

Proteins and peptides suitable for use in this invention may be autologous proteins or peptides, although the invention is clearly not limited to the use of such autologous proteins. As used herein, the term "autologous protein, polypeptide or peptide" refers to a protein, polypeptide or peptide which is derived or obtained from an organism. Organisms that may be used include, but are not limited to, a bovine, a reptilian, an amphibian, a piscine, a rodent, an avian, a canine, a feline, a fungal, a plant, or a prokaryotic organism, with a selected animal or human subject being preferred. The "autologous protein, polypeptide or peptide" may then be used as a component of a composition intended for application to the selected animal or human subject. In certain aspects, the autologous proteins or peptides are prepared, for example from whole plasma of the selected donor. The plasma is placed in tubes and placed in a freezer at about –80° C. for at least about 12 hours and then centrifuged at about 12,000 times g for about 15 minutes to obtain the precipitate. The precipitate, such as fibrinogen may be stored for up to about one year (Oz, 1990).

In that the compositions of the present invention are particularly. suitable for use in tissue adhesion and wound healing, preferred proteins are contemplated. Preferred protein include albumin, fibrinogen or gelatin, with albumin being most preferred.

To select other proteins, polypeptides, peptides and the like for use in the methods and compositions of the present invention, one would preferably select a proteinacous material that possesses one or more of the following characteristics: it forms a solution with a high percentage of proteinaceous material solubilized; it possesses a high viscosity (i.e. about 40 to about 100 poise); it has the correct molecular charge to bind the dye if it is a non-covalent mixture (i.e. anionic protein and cationic dye, or cationic protein and anionic dye); it has the correct amino-acids present to form covalent cross-links (i.e. one or more tyrosines, histidines, tryptophans and/or methionines); and/or it is biocompatible (i.e. from mammalian origin for mammals, preferably from human origin for humans, from canine origin for canines, etc.; it is autologous; it is non-allergenic, and/or it is non-immunogenic).

C. Lipids

In certain embodiments, the present invention concerns novel compositions comprising at least one lipid associated with at least one photosensitizer. It is contemplated that lipids can chemically react with photosensitizers, particularly at double bonds. Thus, it is contemplated that a photosensitizer and the at least one lipid may form a tissue glue or biomatrix upon photoactivation. Additional one or more lipoproteins embedded or associated with lipids may also react with the photosentizer as described above for proteinaceous compositions in general to form or promote the formation of a tissue adhesive or biomatrix.

A photosensitizer associated with a lipid may be encapsulated in the aqueous interior of a liposome, interspersed within the lipid bilayer of a liposome, attached to a liposome via a linking molecule that is associated with both the liposome and the photosensitizer, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/photosensitizer associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. An example is the lipid dioleoylphosphatidylcholine.

Phospholipids may be used for preparing the liposomes according to the present invention and can carry a net positive charge, a net negative charge or are neutral. Diacetyl phosphate can be employed to confer a negative charge on the liposomes, and stearylamine can be used to confer a positive charge on the liposomes. The liposomes can be made of one or more phospholipids.

In one embodiment, the lipid material is comprised of a neutrally charged lipid. A neutrally charged lipid can comprise a lipid without a charge, a substantially uncharged lipid or a lipid mixture with equal number of positive and negative charges.

In one aspect, the lipid component of the composition comprises a neutral lipid. In another aspect, the lipid material consists essentially of neutral lipids which is further defined as a lipid composition containing at least 70% of lipids without a charge. In other aspects, the lipid material may contain at least 80% to 90% of lipids without a charge. In yet other preferred aspects, the lipid material may comprise about 90%, 95%, 96%, 97%, 98%, 99% or 100% lipids without a charge.

In specific aspects, the neutral lipid comprises a phosphatidylcholine, a phosphatidylglycerol, or a phosphatidylethanolamine. In another aspect, the phosphatidylcholine comprises dioleoylphosphatidylcholine.

In other aspects the lipid component comprises a substantially uncharged lipid. A substantially uncharged lipid is described herein as a lipid composition that is substantially free of anionic and cationic phospholipids and cholesterol. In yet other aspects the lipid component comprises a mixture of lipids to provide a substantially uncharged lipid. Thus, the lipid mixture may comprise negatively and positively charged lipids.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Liposome-mediated oligonucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection. Thus, it is contemplated that a liposome/photosensitive dye composition may be used to deliver additional materials, including active, therapeutic or diagnostic agents to a tissue. In one aspect the additional material is comprised in a lipid construct, such as a liposome.

In certain embodiments of the invention, the lipid may be associated with a hemagglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. Such expression vectors have been successfully employed in transfer and expression of an oligonucleotide in vitro and in vivo and thus are applicable for the present invention. Where a bacterial promoter is employed in the DNA construct, it also will be desirable to include within the liposome an appropriate bacterial polymerase.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY—YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. Phospholipids (Avanti Polar Lipids, Alabaster, Ala.), such as for example the preferred neutral phospholipid dioleoylphosphatidylcholine (DOPC), is dissolved in tert-butanol. The lipid is then mixed with the photosensitizer, proteinaceous material, agent and/or other component(s). Tween 20 is added to the lipid mixture such that Tween 20 is 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline. The average diameter. of the particles obtained using Tween 20 for encapsulating the lipid with the oligo is 0.7–1.0 μm in diameter.

Alternatively liposomes can be prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures: the method of Bangham et al. (1965), the contents of which are incorporated herein by reference; the method of Gregoriadis, as described in *Drug Carriers in Biology and Medicine*, G. Gregoriadis ed. (1979) pp. 287–341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50–200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

D. Formulations and Application

The present invention is generally directed to compositions comprising at least one photosensitizer. The photosensitizer may be used without an additional proteinacous, lipid, and/or active agent element, as endogenous lipids, proteins, polypeptides and peptides may provide a reactable component upon photoactivation to form an adhesive tissue glue or biomatrix for delivery of additional components to a tissue. However, it is preferred that the composition comprise at least one proteinaceous and/or lipid material in combination with a photosensitizer. Although not intended exclusively for use in tissue sealing, the compositions of the invention may be referred to as a tissue or surgical adhesive, glue, or sealant, or a wound sealant. All of the foregoing terms are used herein to describe a combination of components capable of adhering, sealing, closing, apposing or otherwise joining, two or more soft tissue elements. A tissue glue thus preferably functions to promote, catalyze or otherwise generally cause the formation of covalent bonds between tissues, such as the edges of a wound or surgical incision, so that it promotes the formation of a proteinaceous framework between tissue elements allowing the formation or reconstruction of a biological seal.

The compositions of the invention will generally comprise at least one biocompatible lipid, protein, polypeptide, peptide and/or active agent containing composition in combination with an amount of at least one biocompatible photosensitizer effective to promote the formation of an adhesive upon photoactivation. In other aspects, the combination will comprise covalent and/or non-covalent conjugation of the lipid(s), protein(s), polypeptide(s), peptide(s) and/or active agent(s) with the photosensitizer(s). In certain embodiments, the combination of proteinaceous, active agent and/or lipid composition and at least one photosensitizer is a mixture wherein the components are not or essentially not covalently bonded to each other prior to photoactivation. In other embodiments, part or all of the proteinaceous, active agent and/or lipid composition is covalently bonded to the at least one photosensitizer, or to each other in any combination. In certain aspects, the conjugation between one or more proteinaceous, active agent and/or lipid components of the composition and the at least one photosensitizer is a direct conjugation, such as at least one covalent bond without additional linking moietie(s) connecting a lipid, active agent, protein, polypeptide or peptide to the photosensitizer, or to each other in any combination.

In other aspects, at least one additional atom or chemical group comprises at least one linking moiety that covalently connects the lipid(s), active agent(s), protein(s), polypeptide(s) and/or peptide(s) to the photosensitizer, or to each other, in any combination. It is preferred that such a linking moiety is short, i.e., that it separates the at least one lipid, active agent, protein, polypeptide, peptide and/or photosensitizer by about 10, 9, 8, 7, 6, 5, 4, 3, 2, or 1 atoms in a chain, irrespective of any additional side chemical groups that may be attached to the chain. However, longer linking moieties are contemplated. In particular embodiments, one or more selected lipids, active agents, proteins, peptides and/or polypeptides may also be conjugated to each other in the proteinaceous and/or lipid composition. Chemical linking moieties and chemically bonding such a moiety to proteinaceous material and other components are known to those of ordinary skill in the art (see U.S. Pat. Nos. 5,880,270, 5,856,571, 5,547,667, 5,387,578, 5,306,809 and 4,680,338, each incorporated herein by reference). Linkers to lipids and other molecules are described in U.S. Pat. No. 5,840,674, incorporated herein by reference.

The novel compositions of the present invention may be formulated with any pharmacologically acceptable medium or diluent. Biocompatible formulations of lipid, protein, polypeptide, peptide and/or active agent containing compositions and photosensitizers may variously include aqueous solutions and physiological buffers and other agents, such as stabilizers and fatty acids. The protein content of the composition may be adjusted according to the viscosity of the composition desired, and in view of the intended use of the composition and the nature of any tissues to which it may be applied. In general, photosensitizer, lipid, active agent, protein, polypeptide and/or peptide formulations of the correct viscosity are limited by the solubility of the proteinaceous, active agent, photosensitizer and/or lipid material. The solution is to be thick enough to stay in the wound and not so thick as to clot in the needle as it is being applied. The amount of each photosensitizer needed is proportional to the protein and/or lipid concentration and will be determined for each application. The proportion of protein to photosensitizer is important, as too much photosensitizer will consume the oxygen radicals before they have a chance to cause a reaction and insufficient radicals will not generate enough reactive species to complete the reaction. The lifetime of the singlet oxygen will also vary with the concentration of the photosensitizer and of the solvent used. These variables can be determined for each application without undue experimentation by those of skill in the art.

In certain embodiments, a preferred range of viscosity is from about 40 to about 100 poise, with a range of about 80 to about 100 poise being particularly preferred. However, various viscosities are contemplated, including but not limited to, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100 poise, and any range derivable therein.

In preparing a composition intended for application to a particular selected tissue, it is contemplated certain advantages may be gained by employing a lipid, active agent, protein, polypeptide and/or peptide known to be present within that selected tissue. One example of such a combination is the use of the crystallin lens protein in compositions intended for application to the eye.

In certain aspects, ranges of composition that is applied includes, but is not limited to, of from about 10 mg glue composition/cm$^2$ to about 500 mg /cm$^2$. A more preferred range would be of from about 20 mg/cm$^2$ to about 100 mg/cm$^2$. In certain embodiments, the range of composition that may be applied includes, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, to about 500 mg/cm$^2$ or greater, and any range derivable therein.

The biocompatible proteinaceous, active agent, lipid and/or photosensitizing components of the novel compositions disclosed herein may be in the form of a single component system such that they form a single composition. Within the single composition, the components may be physically separate or they may be physically combined, for example, by the covalent attachment of a photosensitizer to a lipid, active agent, protein, polypeptide or peptide. This attachment may be achieved by any one of a variety of chemical coupling means known to those of skill in the art including, for example, the use of reducers, oxidants, acids, bases and other chemically reactive species such as $HCO_3$.

Alternatively, the compositions of the present invention may be in the form of double, triple or greater number component systems where both individual components are stored separately until use. In the latter case, a single composition may still be formed by mixing, or combining, the lipid, protein, polypeptide, peptide and/or active agent containing and photosensitizing components some time prior to use. Alternatively, each component may be applied separately to the tissue area, or wound to be joined, such that the active composition will only be formed on irradiation of the tissue itself, ie., it is only formed in situ. It will be understood that all such alternatives and combinations thereof fall within the scope of the present invention.

It is contemplated that the proteinaceous, active agent and/or lipid composition may comprise 1, 2, 3, 4, 5 or more selected lipids, active agents, proteins, polypeptides and/or peptides. One or more of the selected lipids, active agents, proteins, polypeptides and/or peptides may be conjugated with the photosensitizers described herein, or those that are known to those of ordinary skill in the art. Thus, it is contemplated that the compositions and methods disclosed herein may be combined, with, for example, additional photosensitizers and materials including but not limited to those disclosed in U.S. Pat. Nos. 5,552,452 and 5,913,884, each incorporated herein by reference.

Further aspects of the invention concerns kits for use in forming an adhesive connection between biological tissues or forming a biomatrix. Such kits will include a light-protected container comprising a biocompatible photosensitizer and a biocompatible lipid, protein, polypeptide, peptide and/or active agent containing composition as described above. It is particularly important that the photosensitive component be kept in the dark, i.e., in the light-protected container. Photosensitizers included in the kits in powdered form need to be provided in water and water vapor tight containers and will be stored in refrigerated environments, for example from about 4° C. to as cold as about −80° C. However, as with the compositions, the kit may be in the form of a double, triple, or greater number component kit system where the components are stored separately until use. In this case, there is no requirement that the protein, polypeptide or peptide containing component also be stored away from the light, and it may kept in a separate container of any form. However, it is preferable that lipids and light sensitive agents be stored away from the light.

Suitable containers are contemplated to include light-protected tubes; plastic, dark glass or otherwise light-protected bottles, or light-tight foil wraps. Such containers may also comprise a means to apply the adhesive to the tissue, for example a collapsible tube, or a glass container with a plunger device to dispense the adhesive comprising a syringe like device. It is contemplated that such a device may comprise a syringe in which the lipid, proteinaceous material, active agent and/or photosensitizer solutions are separated by a plate that contains serrations which will penetrate the photosensitizer containing compartment and then allow mixing of the contents of that compartment with the contents of the protein containing compartment. In that the operation of the kits will generally rely on photo-oxidative mechanisms and singlet oxygen generation, one may wish to store the photosensitizer,the lipid, protein, polypeptide, peptide and/or active agent containing compositions in a high oxygen atmosphere or in an atmosphere which has a higher oxygen concentration or tension than usual. As with any biological formulation, it is advisable to store these kits under refrigeration, such as at 4° C.

D. Tissue Welding

In still further embodiments, the present invention concerns methods for forming an adhesive connection between biological soft tissues or filling in damage to other tissues. The invention may be used in surgical applications where precise adhesion is necessary and where the application of sutures or staples is inconvenient or less effective than tissue adhesive. The adhesive of the present invention has uses in closing large wounds and tissue defects as in filling in a defect caused by debridement. Another use is as an artificial skin or covering agent to cover large, oozing surfaces inside or outside the body. Other uses include the repair of large, internal areas which are raw, or friable and which leak fluid and blood; reinforcement for a sutured anastomosis, thus rendering it water tight and bacteria tight; apposing parts of the body which are normally held together by surface tension such as the lung and chest wall; and to seal leaking blebs in the lung which are very difficult to treat.

All such methods and procedures can be described as "welding tissue", "tissue welding", a method to "weld tissue", etc. In certain embodiments, the method involves application of the tissue glue to at least one tissue. The "at least one tissue" may be a single tissue type, or a multiple tissues closely associated to form essentially one discernable mass, layer, section or body of tissue to which the tissue glue may be applied. In other aspects, the "at least one tissue" may be a surface area, face or region of a tissue mass, layer, section or body of tissue. In certain aspects, the tissue welding process creates or promotes adhesion of the at least one tissue to at least a second tissue. The "at least a second tissue" may be a single tissue type, or a multiple tissues closely associated to form essentially one or more discernable mass, layer, section or body of tissue that is separated from the "at least one tissue." In other aspects, the "at least a second tissue" may be a surface area, face or region of a tissue mass, layer, section or body of tissue. Thus, it is possible that the tissue weld will create or promote an adhesion between two or more ends, faces, surfaces areas, regions or the like of a single tissue mass or body of tissue. In certain aspects, tissue glue or one or more components of the tissue glue composition may be applied to either or both the at least one tissue and the at least a second tissue. A non-limiting example of such a tissue weld would be to connect two ends of an intestinal sheet of tissue to form a tube. Another non-limiting example would be to tissue weld an incision or tear in the skin or muscle. Another non-limiting example, would be to weld three or more separated pieces of tissue together, wherein each of the tissue pieces is a different type of tissue. Of course, one of ordinary skill in the art will recognize that there are a multitude of possible combinations of tissue welds that may be made in light of the disclosures herein.

To perform such a tissue welding method or procedure, one would first prepare a composition as described herein and then apply the composition to the tissue(s) to be connected to form a tissue adhesive combination. One would then irradiate the tissue adhesive combination, i.e., apply electromagnetic radiation to this area, in a manner effective to promote the formation of an adhesive connection between the tissues. The formation of an adhesive connection will be achieved by the photo-oxidative effects of singlet oxygen generating proteinaceous cross-links between the amino acid components of the composition and/or tissue.

The present invention also encompasses methods for tissue closing or wound healing wherein the actual preparation of a separate lipid, active agent, protein, polypeptide and/or peptide containing composition is not necessary. Such methods utilize the lipids, polypeptides, peptides and/or proteins located naturally within the tissue area as in situ protein containing compositions. To form an adhesive connection between biological tissues in this manner one would form a biologically effective amount of a tissue adhesive combination at the tissues by applying only the photosensitizer and/or active agent component(s) to the tissues. In certain aspects, ranges of glue composition that is applied includes, but is not limited to, of from about 10 mg glue composition/cm$^2$ to about 500 mg /cm$^2$. A more preferred range would be of from about 20 mg/cm$^2$ to about 100 mg/cm$^2$.

One would then again apply electromagnetic radiation the tissue adhesive combination thus formed in a manner effective to promote the formation of an adhesive connection between the tissues.

In either of the methods described above, the amount of the composition used will, naturally, be dependent on the tissue(s) to which it is being applied and on the size and nature of the wound or incision to be closed or the distance between the tissues to be apposed. The determination of the appropriate amount of the composition to be, applied will be known to those of skill in the art in light of the present disclosure. Likewise, the application of the electromagnetic radiation will also be adapted to suit the particular circumstances of operation. It is generally envisioned that the time for performing a tissue closure procedure in accordance herewith will be less than five minutes in total. For example, the closure of an incision of about 5 mm in length is contemplated to require in the order of 1 to 2 minutes. The time of irradiation of the composition will depend not only on the size of the lesion and the desired end strength of the bonds (i.e., greater irradiation produces greater bond formation), but also on the composition itself, the characteristics of the wound, and the practitioner's preference.

A particular advantage of the present invention is the precision with which it can be used. Other glues that have been used stick wherever they are applied and much care must be taken to avoid the glue spilling over into areas where it is not desired. In the present invention, the glue is activated only where the practitioner applies the laser light and this can be a very small area, i.e., on the order of about 2 mm diameter. Thus any excess glue can be ignored or washed off. In this way the area of actual tissue adhesion is precisely controlled and is determined by the steadiness of the application of the laser energy. It is contemplated that even more precision is possible through the application of the laser energy by electronically controlled means. The glue composition may also be applied in layers to gradually fill in a defect or gradually strengthen the wound. The electromagnetic radiation may be delivered within the glue matrix through special delivery devices or simply applied on top of the glue layer.

The electromagnetic radiation necessary to achieve photoactivation will generally have a wavelength from about 10 nm to about 810 nm and will be within the visual, infra red or ultra violet spectra. The radiation will be supplied in the form of a monochromatic laser beam or other form of electromagnetic radiation source. The choice of energy source will generally be made in conjunction with the choice of photosensitizer employed in the composition. For example, an excimer laser is suitable for refractive surgeries. Suitable combinations of lasers and photosensitizers will be known to those of skill in the art, and are exemplified, but not limited to, those shown in Table 2.

TABLE 2

| Photosensitizer | Laser Source Wavelength |
| --- | --- |
| Any tetrapyrrole including but not limited to: hematoporphyrin, chlorin, bacteriochlorin, phthalocyanine or naphthalocyanine | Blue diode (460 nm) |
| Rose bengal or riboflavin | Blue-Green Argon 488–514 nm |
| Porphyrins or cyanines | Green diode (532 nm) |
| Hematoporphyrin, protoporphyrin, other porphyrins, toluidine blue, malachite green, azure A, azure B, brilliant green, patent blue VF | Red diode (630 nm) |
| Chlorins, chlorin$_e$6, tetrahydroxyphenyl chlorin, methylene blue, Janus green, | Red diode 660 nm |
| Benzoporphyrin derivative | Red diode (690 nm) |
| All of the dye listed under red diodes | Tunable dye laser (600–700 nm) |

Tunable dye lasers are also used with the present invention. These lasers can be tuned to emit generally any wavelength within a broad spectrum and allow for exact matching of dye and laser wavelength. In other embodiments, the source of irradiation may be non-laser light (i.e., polychromatic light) from an incandescent, fluorescent or other source which could be used to activate the glue/matrix composition. In particular embodiments the non-laser light source may be from a xenon bulb devices using filters and liquid light guides to deliver defined wavelength ranges depending on the filter. Application of these technologies will be known to those of skill in the art.

The present invention is envisioned to be suitable for use in a variety of surgical embodiments where one desires to seal, close, appose or otherwise join two or more portions of soft tissue, or to fill in cavities. or damage to soft or hard tissues. The invention is considered to be particularly suitable for use in microsurgery, such as, for example, in surgical operations or maneuvers concerning the eye, small vascular tissue, gastrointestinal tract, nerve sheaths, small ducts (e.g., urethra, ureter, bile ducts, thoracic duct) or even the inner ear, teeth or gums. It can be used in areas where use of a suture in a non-sterile part of the body would help foster an infection such as in the oral cavity. The invention may also be used in conjunction with ordinary sutures to provide a better cosmetic closure, such as to provide a smooth surface on top of the suture surface. It is particularly suitable for procedures involving laparoscopic operations or interventions such as laparoscopic (LP) cholecystectomy, LP nephrectomy, LP thoracic procedures, LP appendectomy, LP hernia repairs, LP tubal ligations and LP orbital surgeries. The present invention will also be useful in retractive surgeries. However, these examples are clearly not limiting and the use of the methods and compositions described herein in connection with any type of wound closure or surgical procedure is encompassed by the invention.

In yet further embodiments, the present invention concerns methods for cross-linking proteinaceous compounds, active agents and/or lipids. Such methods comprise forming an effective amount of a proteinaceous material or lipid cross-linker combination at the proteins, polypeptides, peptides, active agents and/or lipids, to be cross-linked and irradiating the combination with electromagnetic radiation in a manner effective to promote the formation of cross-links between the proteins, polypeptides, peptides, active agents and/or lipids. The at least one proteinaceous compound, active agent and/or lipid cross-linker combination may be formed by preparing a composition in accordance herewith and applying the composition to the materials to be cross-linked, or by applying only the photosensitizer component itself to the proteins, polypeptides, peptides, active agents and/or lipids. In certain embodiments, dimers, such as an albumin dimer may form during crosslinking. In further embodiments, albumin-collagen cross-linking may occur. It is also contemplated that in certain embodiments, type I and/or type II photoprocesses may contribute to the process of crosslinking. The choice of electromagnetic radiation and photosensitizer will be coordinated as discussed above and as exemplified by the combinations listed in Table 2.

Cross-linking proteins in this manner is contemplated to be of use in a variety of non-clinical embodiments including but not limited to, for example, in cross-linking proteins for use in chromatographic columns or beads, the immobilization of antibodies or antigens for diagnostic or purification purposes, or for the fixing of proteins for microscopy.

E. Biomatrix Uses

It is contemplated that one or more photosensitizer, proteinaceous material, lipid and/or active agent (e.g., cells, drugs, nucleic acid vectors, antigens, etc.) may be combined in the compositions and methods of the present invention to form a biomatrix for delivery of one or more active agents to various tissue types. In certain embodiments, it is contemplated that the active agents may comprise one or more therapeutic or diagnostic agents. Active agents include, but are not limited to, one or more chemicals; drugs; proteins, polypeptides and peptides including antibodies; hormones; nucleic acids including antisense oligonucleotides and recombinant nucleic acid constructs; nutritional substances; antigens; and combinations thereof. These agents may be mixed with or covalently bonded to either the proteinaceous component, lipid component or dye component of the composition. The agent may be used alone and without the other non-dye components.

In certain embodiments, the agent is slowly released from the biomatrix/tissue glue. The composition and light exposure may be manipulated to allow optimum duration of the composition and therefore drug delivery. Such adjustments of the consistancy and biodegradable nature of the matrix is within the ability of one of ordinary skill in the art in light of the disclosures herein. In a particular embodiment, the biologic matrix may be loaded with a drug to enhance or retard wound healing. The composition may be used to retard wound healing in operation where scarring of an artificially created tract, shunt, and or fistua would not be desirable. The matrix may deliver a cytotoxic or cell growth inhibitory material, including but not limited to 5-fluorouracil or mitomycin. Such cytotoxic drugs may be used in various clinical applications, such as is used in glaucoma filtration surgery, or controlling the growth of skin keloids. Another use would be in proliferative vitreoretinoapthy where the matrix may be applied to slowly release an agent such, including but not limited to vitamin E, that may inhibit or eliminate the proliferation of certain cells such as vitamin E (Larrosa J M. Et al., 1997). The matrix may also be used to deliver cortico steroids or non-steroidal anti-inflammatory agents, for applications including but not limited to, control of post-operative inflammation, such as in uveitic eyes after intra-ocular surgery or surgery of the nervous system to control post-operative edema and inflammation. The composition may also be used to deliver antibiotics to a difficult to reach space, including but not limited to the vitreous cavity of the eye or to areas of chronic infection such as osteomyelitis. The matrix may also be used in drug or gene therapy to deliver long term depots of an agent over a long span of time to a specific area/space. Particular agent that are contemplated include anti-cancerous medications. In such uses the matrix would spare systemic exposure to the pharmaceutical agent and allow concentrated exposure for a relatively enhanced period of time. Again, this period of time may be adjusted based on composition of the matrix and level of light activation.

In one embodiment, the active agent is an antigen that is contacted with a host organism's immune system to promote immunity, or in some cases, tolerance to the antigen. Thus, a tissue glue or biomatrix vaccine is contemplated.

In a preferred embodiment, the agent is a hormone involved in tissue growth or repair. Much progress has been made in identifying and characterizing the multitude of growth factors involved in the various stages of the healing process. Recombinant DNA technology has led to the ability to produce these polypeptides in a pure form without the necessity of isolating them from human material. Consequently many workers have attempted to use these recombinant growth factors to stimulate processes of tissue repair and remedy deficiencies in wound healing.

However it was quickly discovered that in order to be effective these growth factors should remain in the tissue defect for a sufficiently long time to allow the cellular process of healing to take place. This time should be at least about one hour, though longer periods such as 48 hours and greater are preferable. However when growth factors are directly applied into tissue they remain only in position only for very short times, sometimes only minutes.

It may be that there are many cases where the actual tissue binding of the growth factor laser activated glue will be a distinct improvement, for instance allowing much more movement of the affected area without dislodging the glue. Examples of growth factors that may be used as agents in combination with the tissue glue include, but are not limited to, transforming growth facto beta (isoforms 1, 2, or 3) (Foitzik et al., 1999; Yamamoto et al., 2000), basic fibroblast growth factor (Wang, 1996), epidermal growth factor (Sheardown et al., 1997), vascular endothelial growth factor (Chawla et al., 1999), nerve growth factor (Mohammad et al., 2000), acidic fibroblast growth factor (Sellke et al., 1996), insulin like growth factor (Prisell et al., 1997), heparin binding growth factors (Sakiyama-Elbert & Hubbell, 2000), brain-derived neurotrophic factor and glial cell line-derived neurotrophic factor (Vejsada et al., 1998), platelet-derived growth factor (Khouri et al., 1993), leukemia inhibitory factor (Leong et al., 1999) and combinations thereof. Examples of tissues that may be treated in this fashion include, but are not limited to, skin (Pierce et al., 1988), bone (Yamamoto et al., 2000), peripheral neurons and axons (Mohammad et al., 2000; Vejsada et al., 1998), central neurons and axons (Cheng et al., 1998), cartilage (Rayan & Hardingham, 1994), blood vessels (Chawla et al., 1999), cornea (Sheardown et al., 1997). Additional bioactive substances and methods of using a solder for delivery of them is described in U.S. Pat. No. 5,713,891, incorporated herein by reference.

In other aspects, the agent is one or more living cells. The cells may be shaped by the biomatrix into a monolayer or other conformation. It is preferred that the biomatrix degrades in the tissue or organism it is contacted with to allow the transplanted cells assume an optimum shape or function in the tissue or organism. The biomatrix may be formed in vitro or in vivo, and may serve as a reservoir of nutrients for living cells, either for cells contained as an agent or for the tissue(s) to which the biomatrix is applied. Thus, the biomatrix may serve as a type of solid or semi-solid cell culture medium or therapeutic wound dressing. In certain embodiments, the biomatrix may be applied to wounds that have traditionally healed poorly, including but not limited to cartilage, poorly vascularized areas, areas of lost tissue such as, for example, skin lost due to burns. When applied to a tissue, it is contemplated that the biomatrix can modulate the growth and morphology of the transplanted cells, particularly when the biomatrix comprises various growth factors, hormones, adhesive compositions that attract the transplanted cells. In certain embodiments, the biomatrix may allow, or even promote, the infiltration of host cells into the composition after it is applied to a tissue.

The biomatrix may be varied in composition to be impermeable to additional nutrient or aqueous media, or may allow such materials pass into or through the biomatrix. In certain embodiments, it is preferred that the matrix is impermeable after photoactivation, such as use as a tissue glue in organs including but not limited to the eye, gastrointestinal tract, blood vessels, etc.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Photodynamic Tissue Adhesion with Chlorin$_{e6}$ Protein Conjugates

This example demonstrates that the use of a chromophore, such as for example, chlorin$_{e6}$ ($C_{e6}$) may be effective in cross-linking proteins by a photodynamic mechanism. Covalent conjugates between $C_{e6}$ and proteins used as laser-activated solders form stronger tissue bonds than non-covalent mixtures. The finding that addition of sodium azide to the glue preparation reduces the leaking strength by more than 50% is attributed to quenching of singlet oxygen.

Preparation of Conjugates: $C_{e6}$ was obtained from Porphyrin Products (Logan, Utah), N-hydroxy succinimide (NHS), dicyclohexylcarbodiimide, bovine fibrinogen, bovine serum albumin (BSA), and gelatin were from Sigma (St. Louis, Mo.). Frozen, nonpreserved, human cadaveric eyes were obtained from the Illinois Eye Bank (Chicago). The reaction sequence used to attach the $C_{e6}$ molecules to the proteins covalently is shown in FIG. 1. All reactions were performed in the dark at room temperature. The NHS ester of $C_{e6}$ was prepared by reacting 1.5 equivalent of dicyclohexylcarbodiimide and 1.5 equivalents of NHS with 1 equivalent of $C_{e6}$ in dry dimethyl sulfoxide (DMSO) for 24 hr and was frozen in aliquots for further use. The concentration of the $C_{e6}$NHS in DMSO was 100 mM. Proteins were dissolved in 0.1 M NaHCO$_3$ buffer (pH 9.3). For BSA the concentration was 500 mg/ml, for fibrinogen 100 mg/ml, and for gelatin 200 mg/ml. A fivefold molar excess of $C_{e6}$NHS ester in DMSO was added to the protein solution, which was allowed to stand overnight. The crude conjugate-solution was then dialyzed twice against 5l phosphate-buffered saline (PBS) to remove unconjugated $C_{e6}$ and DMSO. The conjugate between BSA and $C_{e6}$ could be prepared easily and dialyzed to give a viscous dark green solution.

Mixtures of $C_{e6}$ and proteins were prepared by dissolving $C_{e6}$ in 0.1 M NaOH to form a 100-mM solution, adding the requisite amount to the protein solution in PBS and neutralizing with 0.1 M HCl. Conjugates were characterized by absorption spectroscopy after suitable dilution in PBS.

Conjugates, which contained approximately 6 mM BSA (400 mg/ml), had the appropriate consistency and viscosity for using as solders in incisions. The conjugate between gelatin and $C_{e6}$ could not be prepared in a high enough concentration yield a sufficiently viscous solution. The conjugate between fibrinogen and $C_{e6}$ was substantially aggregated and unsuitable for use as solder. To explore the effect of these proteins on the weld strength, gelatin was added to BSA–$C_{e6}$, and fibrinogen was mixed with BSA–$C_{e6}$ and with free $C_{e6}$. The compositions of the conjugates and mixtures that were used as solders are shown in Table 3. For Table 3, $C_{e6}$ and protein concentrations were measured by absorption spectroscopy after appropriate dilutions in 0.1 M NaOH and 1% sodium dodecyl sulfate using extinction coefficients for $C_{e6}$ of 150,000 at 400 nm, and for protein of 47,000 at 280 nm. Protein and $C_{e6}$ data are in millimolar.

TABLE 3

DETAILS OF THE CONJUGATES
AND MIXTURES USED AS SOLDERS

| Composition | Protein | $C_{e6}$ | Protein/$C_{e6}$ Ratio |
|---|---|---|---|
| BSA – $C_{e6}$ conjugate | 5.2 | 6.2 | 0.84 |
| BSA + $C_{e6}$ mixture (1:1) | 5.3 | 5.4 | 0.98 |
| BSA + $C_{e6}$ mixture (2.5:1) | 5.9 | 2.3 | 2.56 |
| BSA – $C_{e6}$ conjugate + BSA | 6.0 | 1.5 | 4 |
| BSA – $C_{e6}$ conjugate + gelatin | 3.2 | 0.8 | 4 |
| Fibrinogen + $C_{e6}$ mixture | 3.3 | 1.6 | 2.06 |
| BSA – $C_{e6}$ conjugate + fibrinogen | 4.1 | 1.6 | 2.56 |
| R-5-P + fibrinogen | 0.9 | 5.7(r-5-P) | 0.16(r-5-P) |

Welding Procedure: To measure leaking pressures, an 18-gauge butterfly needle was connected by plastic tubing to a water bottle. The inner pressure in the bottle was controlled by a hand-pumped sphygmomanometer. Nonpreserved cadaveric eyes were defrosted in room-temperature water. The butterfly needle was inserted in the vitreous cavity through equatorial sclera, and the eye was pressurized to 25 to 30 mm Hg. The corneal epithelium was then removed at the wound site, and a caliper set on 5 mm used to make the extent of the incision on equatorial sclera, perpendicular to the limbus. All incisions were placed equidistant from the limbus, and areas of blue or thin sclera were avoided. A perpendicular perforating incision was made with a 15° blade. Incisions were made into the vitreous cavity and extended to the full length using Vannas scissors. The glue was applied in a thin layer to the surface of the wound with a tuberculin syringe and a 30-gauge needle. A small amount was injected within the wound. Argon blue-green laser (488–514 nm; Spectrum K3, HGM Medical Lasers, South Salt Lake City, Utah) at a setting of 0.6 W, 2-mm-diameter spot size, was applied to the wound for 60 to 120 seconds in a continuous back and forth manner using a handheld fiberoptic probe. The exact power output of the fiber was measured using a power meter (model 210; Coherent, Palo Alto, Calif.). Argon laser goggles (Glendale Protective Technologies, Lakeland, Fla.) were worn, which allowed viewing of the fluorescence from the $C_{e6}$ (emission 670 nm). To set the remaining adhesive on the scleral surface, which surrounded the wound, additional laser was applied until loss of fluorescence of the dye, which took another 30 to 45 seconds.

Leaking Pressure: Leaking pressures were then measured using the sphygmomanometer, which was increasingly pressurized in approximately 10-mm Hg increments. Leaking pressure was recorded the moment the wound leaked air or fluid. This procedure was used in all eyes.

The results from the welding studies and determinations of the leaking pressures are shown in Table 4. The total energy delivered varied from 24 to 57 J (60–120 seconds' exposure at powers ranging from 0.4 to 0.52 W). At first, the adhesive strength of the welds produced by BSA–$C_{e6}$ conjugate and BSA+$C_{e6}$ mixture in which the molar ratios of protein to $C_{e6}$ were roughly one to one were compared. However the leaking pressures obtained were low, and more BSA was added to the mixture of BSA+$C_{e6}$ to attain a molar ratio of 2.5:1 protein to $C_{e6}$. The leaking pressure showed a marked increase (Table 4). The protein-to-$C_{e6}$ ratio was then modified to at least 2:1 protein to $C_{e6}$ in the remaining preparations. These results were compared with the preparation when (r-5-P) and fibrinogen were used at a protein-to-r-5-P ratio of 0.16.

TABLE 4

DETAILS OF THE LEAKING STRENGTH
AND APPLIED TOTAL ENERGY
IN THE WELDING STUDIES

| Composition | Eyes | Total Energy Range | Mean Leaking Pressure | Mean Leaking Pressure/ Total Energy Ratio |
|---|---|---|---|---|
| BSA – $C_{e6}$ conjugate | 7 | 39–46 | 78.0 ± 11.9 | 1.75 ± 0.26 |
| BSA + $C_{e6}$ mixture (1:1) | 3 | 24–46 | 63.0 ± 24.3 | 1.77 ± 0.38 |
| BSA – $C_{e6}$ conjugate (2.5:1) | 7 | 24–46 | 127.1 ± 13.4 | 4.04 ± 0.52 |
| BSA – $C_{e6}$ conjugate + BSA | 8 | 24–57 | 207.1 ± 11.1 | 5.59 ± 0.24 |
| BSA – $C_{e6}$ conjugate + gelatin | 11 | 26–53 | 101.8 ± 14.2 | 2.71 ± 0.47 |
| Fibrinogen + $C_{e6}$ mixture | 3 | 24–46 | 39.6 ± 12.5 | 1.1 ± 0.34 |
| BSA – $C_{e6}$ conjugate + fibrinogen | 3 | 24–53 | 35.8 ± 1.8 | 0.93 ± 0.28 |
| Fibrinogen + r-5-P | 6 | 24–46 | 139.5 ± 12.3 | 4.44 ± 0.53 |

Incisions in Table 4 were closed by welding using the solder composition and total energies specified and leaking pressure measured with a sphygmomanometer as described. Total energy is in joules, and leaking pressure is in millimeters of mercury.

Figure 2:
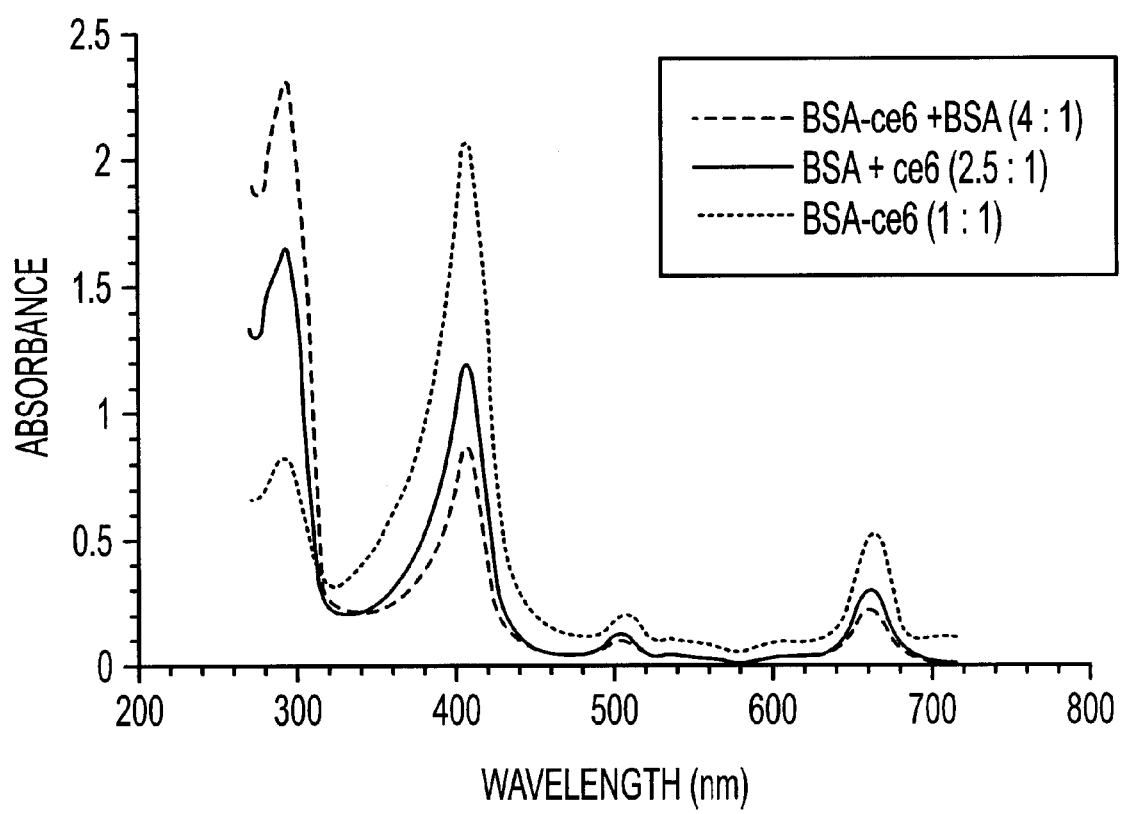
FIG. 2. Absorption spectra of three solder preparations. Solders were diluted in 0.1 M NaOH-1% sodium dodecyl sulfate between 500 and 1200 times.
Figure 3:
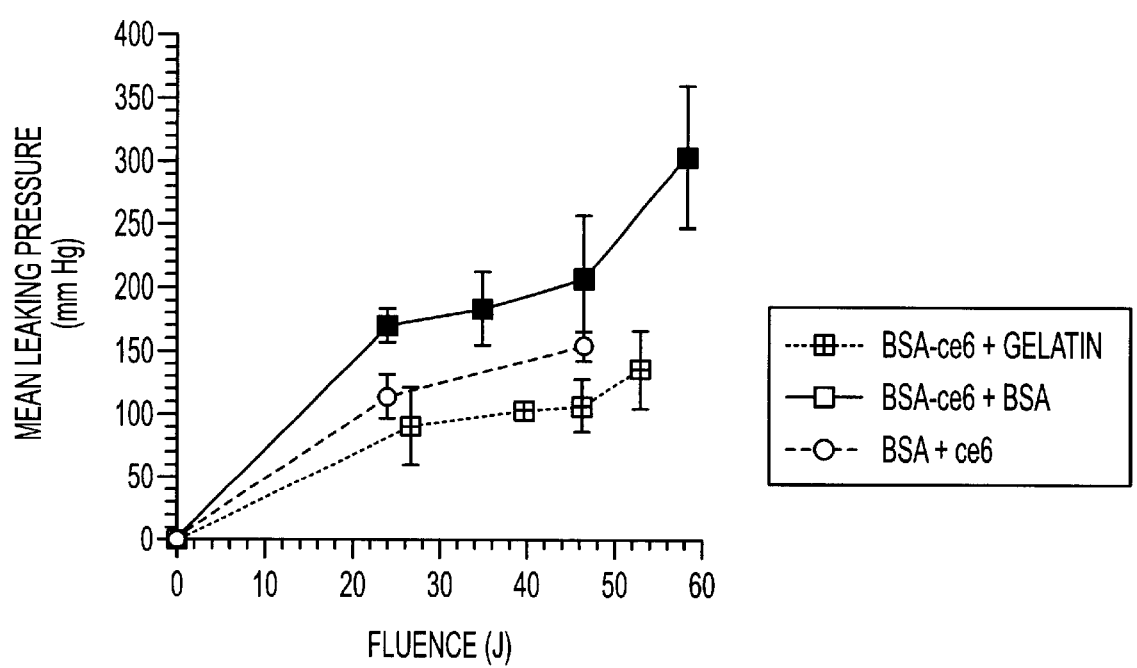
FIG. 3. Fluence dose-response curve showing weld leaking strength. Incisions were closed by using the specified solder preparations and an array of applied total energies. Each point is the mean of leaking pressures from two or three eyes. Bars, ±SEM.

The BSA+$C_{e6}$ (2.5:1) was compared with the BSA–$C_{e6}$ with added BSA, which raised the protein ratio to 4:1. Also investigated was a mixture of BSA–$C_{e6}$ and gelatin that had an overall protein-to-$C_{e6}$ 4:1. The leaking pressure was measured as a function of applied total energy for these three solder preparations, and the results are shown in FIG. 2. Although the green-blue argon laser is frequently used in ophthalmology, it can be readily seen from FIG. 2 that the wavelengths are suboptimal for excitation of $C_{e6}$. A total energy-dependent increase in leaking strength was seen for all three solders, and the order of weld strength was found to be BSA–$C_{e6}$+BSA>BSA+$C_{e6}$>BSA–$C_{e6}$+gelatin. Also investigated as solders were mixtures of fibrinogen with $C_{e6}$ (2:1) and with BSA–$C_{e6}$ (2.5:1). These solders performed not as well as other mixtures, with a leaking pressure of only 30 mm Hg. These results were compared with the preparation consisting of fibrinogen and r-5-P at a ratio of 0.16 protein to r-5-P. The leaking pressure the inventors obtained was similar to that reported (Khadem et al., 1994) (FIG. 3). These various mean leaking pressures were tested for significance with a two-tailed unpaired Student's t-test. The strength of the weld from BSA–$C_{e6}$+BSA was significantly greater than that from fibrinogen+r-5-P (P<0.05), BSA+$C_{e6}$ (2.5:1; P<0.05), BSA–$C_{e6}$ and gelatin (P<0.0005), whereas there was no significant difference between the strengths from fibrinogen+r-5-P and from BSA+$C_{e6}$ (2.5:1), whereas both were significantly stronger than BSA–$C_{e6}$+gelatin (P<0.05).

During the welding procedure there was a visually detectable change in the appearance of the solder, which at first was dark green and became brownish green. Care had to be taken at the ends of the weld where the movement of the handheld fiberoptic probe naturally slowed down in preparation for changing direction. This meant that the center of the incision received less light than the ends and that leakage of the wound started at this point. The consistency of the solder after welding was firm and smooth, and the tissue showed no thermal damage. This could easily be seen if the total energy or the power at which it was delivered was too great. The edges of the wound retracted and started to wrinkle, and the weld failed, because the wound edges were no longer in apposition. Any solder resting on the cornea, that did not receive laser exposure continued to have a liquid, nonadhesive consistency.

EXAMPLE 2

Photodynamic Tissue Adhesion with Chlorin$_{e6}$ Protein Conjugates

The adhesive strength of covalent conjugates to non-covalent mixtures between chlorin$_{e6}$ and proteins in a laser activated soldering process are compared in this example.

The covalent and non-covalent mixtures of C$_{e6}$ photosensitizer contained different molar ratios of albumin, gelatin and fibrinogen. These photodynamic glues were applied to 5 mm incisions along the equatorial sclera and activated with an Argon blue-green laser over a two minutes period. Intra-ocular pressure was increased in 5 mmHg increments until fluid or air escaped from the wound.

The albumin-chlorin$_{e6}$ conjugate welds were significantly stronger than non-covalent mixtures. The albumin–C$_{e6}$ with added albumin provided the highest bursting pressures (mean=207.1 mmHg) in comparison to the other covalent conjugates (mean=88.8 mmHg) and non-covalent mixtures (mean=76.7 mmHg). The order of strength for the most effective photodynamic glues was determined to be: albumin–C$_{e6}$+albumin>albumin+C$_{e6}$>albumin–C$_{e6}$+gelatin–C$_{e6}$.

These results demonstrate that covalent linkages between chlorin$_{e6}$ photosensitizer and protein molecules formed stronger welds than the non-covalent mixtures.

EXAMPLE 3

Tissue Glue as a Slow Release Biomatrix

In this example, a dye containing protein glue mixture containing a phamacologically active amount of the appropriate growth factor will be formulated. Experiments will be conducted in vitro to test the extent of inactivation of the growth factor during the laser activation of the glue. It is expected that although some of the growth factor will be inactivated, enough will remain of the amount introduced to stimulate the tissue repair or wound healing.

Preliminary experiments in the rat cornea show that the laser activated glue remains in the incision for 48 hours, although much less than at time zero. This apparently fulfills the requirement of being a slow release vehicle with a defined rate of biodegradation.

EXAMPLE 4

Growth of Human Fetal RPE Patches on Different Biologic Matrices

The present example demonstrates that a biological matrix, such as formed by a tissue glue composition, may be used in cell transplantation. The present non-limiting example examines the growth pattern, orientation and ease of manipulation of transplanted human fetal RPE (HFRPE) cells different biologic matrices.

Pieces of RPE monolayers, freshly isolated from human fetal eyes at 17–23 weeks gestational age, were patched on the surface of the films (1.5–2.0 rabbit disc diameter) prepared from biodegradable photodynamic glue (J. Khadem et al.,1994) or autologous plasma clot. The cells were studied by light and electron microscopy at different time periods after patching and compared to cultured cells from 2$^{nd}$ passage.

Pieces of HFRPE demonstrated excellent initial attachment to the surface of the biologic glue film. At 48–72 hours new RPE cells appeared at the edges of the monolayer patch. The cells showed orderly growth in a monolayer pattern from high preservation of cellular shape and structure. SEM showed polygonal cells with prominent microvilli on the apex. TEM revealed normal cellular structure with increased nuclear/cytoplasmic ratio. In contrast cultured cells showed less preservation of microvilli and appear elongated. Fresh HFRPE pieces and cultured HFRPE cells attached easily to, the surface of the plasma clot films, retaining their viability at 2 weeks, however no further growth was noted. Both substrates possessed ease of manipulation utilizing vitreal forceps.

This example demonstrates that cells grown on the surface of the biologic glue film from HRFPE patches show highly preserved cellular orientation and morphology and therefore may be useful in transplantation of RPE as a monolayer of primary cells. The consistence of films prepared from the photodynamic biologic glue and plasma clot can be easily handled and manipulated by the vitreal forceps. It is contemplated that the specific tissue glue compositions disclosed herein may be used to grow and shape cells for transplantation, and shape the cells transplanted in tissues.

EXAMPLE 5

A new Model of Retinal Pigment Epithelium Transplantation with Microspheres

In this example, a 3-dimensional culture system for human fetal retinal pigment epithelial (HFRPE) cells in the form of microspheres was developed, and cell growth in the subretinal space evaluated after transplantation. Fibrinogen, which is a powerful stimulator of cell attachment and proliferation (Gray et al., 1993), was used in the matrix. A multicellular spheroid was used, which is 1 form of a 3-dimensional cell culture system (Hoffman, 1993).

Preparation of the matrix: Cross-linked fibrinogen films were prepared under sterile conditions by mixing fibrinogen, 90 mg, and flavin mononucleotide, 1.3 mg (Sigma-Aldrich Corp. St. Louis, Mo.), in 5 mL of deionized water (Khadem et al., 1994). Four drops (~80 pl) of the mixture were spread evenly on the bottom of a 30-cm Petri dish. The mixture was left under UV light for 12 hours. This allowed the formation of 20-to 50-g thick, yellowish, transparent, slightly sticky films that could easily be separated from the bottom of the dish with fine forceps. The film was cut into smaller 1×1-mm pieces that were used for HFRPE monolayer implantation.

Separation and culture of HFRPE cells as microspheres: Human fetal eyes at 17 to 22 weeks of gestation were used in this study. The eyes were enucleated and processed under aseptic conditions. They were subsequently dissected circumferentially posterior to the ora serrata. After gentle removal of the vitreous and retina, RPE cells were separated from the choroid by forceps in large monolayer sheets. No digestive enzymes were used during the separation. After separation, the large HFRPE pieces were cut with microscissors into approximately 1×1-mm pieces. The HFRPE monolayer pieces were placed on the surface of the matrix and incubated in high-glucose Dulfecco modified eagle medium supplemented with 15% fetal bovine serum, levoglutamide, and a combination of penicillin G sodium and streptomycin sulfate. For the first 24 hours, the matrix films bearing the cells were kept attached to the bottom of the culture dish. The films were then easily detached from the dish with forceps and kept in a floating state until microspheres formed. The films bearing the cells became rounded and formed oval or round conglomerates, i.e., microspheres, covered with HFRPE. Microsphere formation took place 7 to 10 days after attachment of HFRPE pieces to the matrix. Three-week-old microspheres were used for transplantation. The growth pattern and morphologic characteristics of HFRPE microspheres attached to the floor of 8-well chamber slides (NUNC, Naperville, Ill.) were studied as in vitro controls.

Transplantation of HFRPE microspheres into the subretinal space: All procedures conformed to the Association for Research Guidelines in Vision and Ophthalmology on the Use of Animals in Ophthalmic and Vision Research as well as The University of Chicago guidelines for animal experimentation. After a standard 3-port vitrectomy, a localized iatrogenic retinal bleb was created with balanced salt solution (He et al., 1993; el Dirini et al., 1992) in 1 eye of 9 albino and 9 pigmented rabbits. A microsphere containing the HFRPE cells was introduced into the vitreous cavity with, a blunt micropipette and transferred to the subretinal space. Nine albino and 9 pigmented rabbits were used as controls. The controls underwent transplantation with a bare matrix of comparable size. Eyes that showed any signs of bleeding during the procedure were excluded from the study. The eyes were evaluated at 7, 14, and 30 days after surgery by indirect ophthalmoscopy and fundus photograph. The rabbits underwent euthanasia, and the eyes were enucleated at 7, 14 and 30 days after the surgery for histological and immunohistochemical studies. Three albino and 3 pigmented rabbits were euthanatized at each point after the transplantation. Controls were followed up and euthanatized similarly. Paraffin-embedded and cryostat sections were used for these studies.

Immunohistochemistry: To identify the donor cells in the pigmented eyes that underwent transplantation, the sections were stained with anti-human monoclonal HLA-ABC antibody specific for human tissue. The antibody showed no cross-reaction with rabbit tissues. Monoclonal anti-human pancytokeratin was used as an epithelial marker. CD5 monoclonal antibody used as an epithelial marker. CD5 monoclonal antibody (Sigma-Aldrich Corp), specific for rabbit panlymphocytes, was used to assess the gross immune response.

For HLA-ABC (catalog number M; DAKO, Carpinteria, Calif.) and CD5 immunostaining, the cryosections were fixed in cold acetone for 10 minutes. Primary antibodies were used in a 1:10 dilution, and the slides were incubated in a moist chamber at room temperature for 1 hour. For monoclonal antipancytokeratin (catalog number C-2562; Sigma-Aldrich Corp) immunostaining, the sections were stained in 10% buffered formaldehyde solution for 10 minutes. The primary antibody was used at a dilution of 1:20 for 2 hours in a moist chamber at 37° C. The secondary antibodies used were sheep anti-mouse immunoglobulin-rhodamine B, 1:10, or immunoglobulin-fluorescein, 1:30 (Rosh Molecular Biochemical, Indianapolis, Ind.), for 1 hour at 37° C. After a final washing in distilled water, the specimens were covered with mounting medium and examined under a microscope (model BH-2; Olympus, Osaka, Japan). Photographs were taken with a camera (model 35AD-4; Olympus, Japan). Film (Ektachromo 320T; Kodak, Rochester, N.Y.) was used for all fluorescence pictures. Monoclonal human anti-CD4 (Sigma-Aldrich Corp) was used as a negative control substrate. The in vitro control specimens were stained similarly for anti-human monoclonal HLA-ABC antibody and for monoclonal antipancytokeratin.

Results: Three albino and 3 pigmented rabbits (6 eyes) were studied in each group that underwent transplantation and in each control group at each period. In total, 36 eyes were studied.

Ophthalmoscopy: 0 to 7 Days: Polygonal human fetal retinal pigment epithelial cells on the outer surface of the microsphere were seen at ×200 magnification. At 7 days after the surgery, there was no hyperpigmentation around the microsphere. The transplanted microsphere appeared as a pigmented subretinal lesion. On day 7, subretinal hyperpigmentation was noted in 2 rabbit eyes in proximity to the transplanted HFRPE microspheres. None of the eyes showed intraocular inflammation.

14 Days: At 14 days after the surgery, there is subretinal hyperpigmentation around the microsphere. Four of 6 eyes showed hyperpigmentation around the transplanted microsphere. In those eyes in which hyperpigmentation was present from day 7, an increase in its size with the formation of pseudopodia was noted around the donor tissue source. No introcular inflammation was seen.

30 Days: At 1 month after surgery, no hyperpigmentation was noted around the microsphere in this pigmented rabbit. Five of 6 eyes showed hyperpigmentation around the microsphere. No ophthalmoscopic evidence of inflammation or infection was noted at the 30-day follow up.

In summary, the extent of hyperpigmentation around the microspheres varied among the eyes, ranging from no hyperpigmentation (7 eyes; 3 albino and 4 pigmented eyes) to prominent hyperpigmentation, with some extending as far as 3 to 4 disc diameters away from the initial donor site.

A total of 11 of 18 rabbits that underwent transplantation showed subretinal hyperpigmentation adjacent to the microspheres. In the control eyes, no subretinal hyperpigmentation was noted. Starting from day 7, prominent whitening due to a large disciform area of chorioretinal atrophy, with no change in size with time, was seen in all control pigmented rabbit eyes around the bare transplanted matrix. Similar chorioretinal atrophy was noted in the control albino eyes at the site of the transplanted matrix.

Hisopathologic characteristics: There were no notable differences noted in the inflammatory response at various times after transplantation. For better assessment of the sections, 3 tissue regions were defined: a region over the microsphere, which included only the microsphere with overlying retina and underlying choroid; a region close to the microsphere, which included the area where the microsphere was always seen with adjacent migrated cells; and a farther region, which included sections where only donor cell monolayer was seen.

In the albino rabbit eye at 7 days after the transplantation, light microscopy showed that the areas corresponding to the transplanted microspheres were composed of a circumscribed region of highly pigmented HFRPE cells. The cells were residing in the subretinal space as thick multilayers. Some of the cells have migrated into the retina. There is local damage to the overlying retina.

An area in close proximity to the retinotomy site showed loss of photoreceptors. Two layers of pigmented cells were seen in the subretinal space. At farther sites, the photoreceptors show better preservation. The pigmented cells formed 2 layers in the subretinal space. Fundus photograph and corresponding light micrographs of fresh frozen sections from an albino rabbit eye 14 days after transplantation showed areas of hyperpigmentation extending from the microsphere. A monolayer of pigmented donor cells grew out from the microsphere in the subretinal space was seen. Migrating cells are seen above the HFRPE monolayer at the level of photoreceptors and appeared rounded. Residing and migrating cells were seen. The retina was artifactually detached during processing.

Loss of photoreceptors was typically noted immediately above and in close proximity to the transplanted tissue. Migration of transplanted HFRPE cells into the overlying neurosensory retina was noted at the site of microsphere implantation. Fragments of the matrix appeared as eosinophilic material between the HFRPE cells. Human fetal retinal pigment epithelial cells were seen in 2 eyes in close proximity to the initial donor tissue at 7 days after the transplantation. At 14 days after the transplantation, the HFRPE cells were identified at farther regions from the microsphere. In both albino and pigmented eyes, the donor cells formed a monolayer in the subretinal space. This corresponded to the hyperpigmentation site that was seen ophthalmoscopically around the microsphere.

The cells forming the transplanted microspheres as well as pigmented cells seen at the subretinal space showed positive immunostaining for HLA-ABC monoclonal antibodies. Migrating human fetal retinal pigment epithelial cells that form a layer above the host retinal pigment epithelium were seen. A negative control was used stained with irrelevant antibody.

Neurosensory retina was preserved above the pigmented cell monolayers located at the distant site from the microsphere.

The area with the transplanted microsphere was also studied by scanning electron microscopy at 30 days after the transplantation in 2 albino eyes. The retina was locally "glued" to the underlying microsphere, and the microsphere appeared flattened. Two layers of RPE could be identified. The cells in the top layer appeared more rounded, with filamentous cell-cell-junctions, possibly representing donor tissue, while the bottom layer showed flatter, more polygonal cells, probably the host RPE. The HFRPE cells that flew out from the microsphere appeared rounded and were of different sizes compared with the host RPE cells. They showed monolayer formation around the microsphere, and they formed long filamentous cell-cell junctions. In some areas, the monolayers were not continuous; and in some areas, only 2 or 3 donor cells were seen.

The cellular response to the transplanted tissue was strictly local and was present around the microsphere, mainly in the underlying choroid. Compared with the controls, there was minimal choroidal thickening with mononuclear cell infiltration beneath the microsphere itself. No inflammatory or lymphoctytic responses were seen in the areas where the HFRPE cells were distributed as monolayers.

A striking difference was noted in the control eyes in which only bare matrix microspheres were transplanted. The subretinal human fetal retinal pigment epithelial microsphere in an albino rabbit eye showed the donor cells that migrated from the initial source. Choroidal infiltration appears less compared with the control. The control pigmented rabbit eye transplanted with bare microsphere matrix had the whole area infiltrated with inflammatory cells.

A markedly thickened, infiltrated choroid was evident under the transplanted matrix, with loss of photoreceptors in the overlying retina. Lymphocytes and other mononuclear cells invaded the entire area of the subretinal space and the retina around the matrix. This could represent a mixed nonspecific inflammatory and immune response. This cellular response was local and was confined to the area of the transplanted bare matrix. The reaction was more severe than in the eyes that underwent HFRPE transplantation. Multiple cells with engulfed eosinophilic material, possibly the matrix, were identified in the area. At 30 days after the surgery, some of the control eyes showed chorioretinal atrophy, with no extracellular matrix present. Immunostaining with CD5 monoclonal antibody, which recognizes rabbit panlymphocytes, showed more intense lymphocytic infiltration in control eyes than in the eyes that underwent HFRPE transplantation. Fluorescence image from an eye that underwent transplantation shows only minimal staining against CD5 compared with the control eye transplanted with matrix only. A negative control was stained with irrelevant antibody.

Subretinal RPE transplantation has shown promise in the rescue of overlying receptors in some experimental degenerative retinal diseases (Tamai, 1996). This may be important in the management of various diseases affecting the RPE. A 3-dimensional culture system offers a new approach for the provision of donor tissue into the subretinal space.

The transfer of the HFRPE cell-containing microspheres into the subretinal space is simple and reproducible. The adjustable size and spherical shape of the donor tissue makes it easy to insert into the subretinal space. Because the HFRPE cells in the model form compact tissue, conglomerates, there is less chance for cell reflux (Wongpichedchai et al., 1992). Other studies (Gouras et al., 1992) of RPE transplantation, there was no evidence of donor cell proliferation or migration in the subretinal space. Some studies indicate that the subretinal space is an immune privileged environment where cell proliferation is kept under strict control. Transplanted cells may need some kind of initial stimulation to migrate or proliferate actively in this environment. Fibrinogen and the 3-dimensional state of HFRPE tissue could contribute to the ability of the cells using the techniques in this example to grow out from the initial source.

Studies done in the laboratory provide indirect evidence of the importance of the modulatory effect of the matrix on cell behavior in the subretinal space. Human fetal retinal pigment epithelial cells grown as microspheres on a synthetic polymer matrix showed notably less potential for subretinal spread compared with cells grown on a fibrinogen matrix (Williamson et al., 1998). Some cell types reexpress their original in vivo characteristics in a 3-dimensional culture and maintain cell-specific functions that are lost in monolayer cultures. The cells in 3-dimensional cultures express increased DNA synthesis and proliferation (Mered et al., 1980; Tamura et al., 1995). Donor cells provided to the recipient as 3-dimensional culture systems show prolonged survival and the ability to migrate from the initial source and establish themselves among the host tissues (Wintermantel et al., 1992; Fawcett et al., 1995). In addition, fibrinogen is a known potent stimulator for cell proliferation and migration (Sporn et al., 1995). Related to it, fibronectin is an important constituent of the Bruch membrane and the surrounding RPE (Campochiaro et al., 1986). Human fetal retinal pigment epithelial cells grown on cross-linked fibrinogen matrix in a 3-dimensional state with tight cell-cell contacts may; become activated (Koller and Papoutsakis, 1995; Olive and Durand, 1994), and possess the potential for migration and proliferation after being brought into the subretinal space. Although there was notable damage to the overlying retina, it appeared to be only local and restricted to the site of the microsphere. The damage can be comparable in size with a large laser bum. The retina appears preserved, however, above the HFRPE monolayers at more distant sites from the microsphere. The growth of HFRPE cells outside the maternal source of donor tissue, shown in these studies, provide an opportunity to transplant microspheres in an extrafoveal region, with secondary spreading to the subfoveal space.

The ophthalmoscopic observation of subretinal hyperpigmentation around the transplanted microspheres corresponded histologically to a monolayer of pigmented cells in albino rabbits. Immunohistochemically, the transplanted cells were identified by staining for HL-k-ABC antibody, and similarly showed migrating HFRPE cells from the initial source with monolayer formation close to the transplanted microsphere.

All control eyes transplanted with bare matrix showed a notably higher inflammatory response and increased lymphocytic infiltration compared with the HFRPE transplanted eyes. Retinal pigment epithelium can modulate the functions and behavior of other cells, such as lymphocytes, vascular endothelial cells, and macrophages (Liversidge et al., 1994; Liversidge et al., 1993; Sakamoto et al., 1995). Recent studies (Ochalek and von Kleist, 1994) have shown that some tumor cells grown as spheroids show increased resistance to lymphocyte lysis and inhibition of lymphocyte penetration compared with the cells grown as monolayers. Human fetal retinal pigment epithelial cells transplanted as multicellular spheroids, i.e. microspheres, may similarly possess lymphocyte inhibitory qualities. Retinal pigment epithelium cells have been shown to release transforming growth factor β family proteins (Anderson et al., 1995) that have immunosuppressive functions and that can inhibit neovascularization (Yoshimura et al., 1995; Seaton et al., 1994). In addition, cell types grown in a w-dimensional culture system show increased leves of intracellular cytokines, including transforming growth factors. Human fetal retinal pigment epithelial cells cover the matrix, possibly preventing its direct contact with the subretinal tissues, resulting in less intense inflammation compared with controls. Some studies (Tamai, 1996) explain he rescuing effect of RPE transplantation to cytokine release by healthy donor cells. Three-dimensional cultures of HFRPE cells may be a better source of the cumulative release of different trophic cytokines (Ness et al., 1994), compared with monolayers, due to the high accumulation of healthy cells;

In conclusion, the provision of donor cells into the subretinal space as microspheres is reproducible and technically easy, and it may decrease the chances for iatrogenic damage to the retina. The donor cells can spread and survive in the subretinal space for at least 1 month.

All of the compositions and/or methods and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Albes, Kretteck, Hausen, Rohde, Haverich, Borst, "Biophysical properties of the gelatin-resorcin-formaldehyde/glutaraldehyde adhesive," *Ann. Thorac. Surg.*, 56:910–915, 1993.

Anderson, Guerin, Hageman, Pfeffer, Flanders, "Distribution of transforming growth factor-beta isoforms in the mammalian retina," *J. Neurosci Res.*, 42:63–79, 1995.

Ashton, Oz, Lontz, et al., "Laser-assisted fibrinogen bonding of vascular tissue," *J. Surg Res.*, 51:324–328, 1991.

Bachor, Shea, Gillies, Hasan, "Photosensitized destruction of human bladder carcinoma cells treated with chlorin e6-conjugated microspheres," *Proc. Natl., Acad. Sci. USA*, 88:1580–1584, 1991.

Back, Kopchok, White, Cavaye, Donayre, Peng, "Nd:YAG laser-welded canine arterivenous anastomoses," *Lasers Sur. Med.*, 14:111–117, 1994.

Bass and Treat, "Laser tissue welding: a comprehensive review of current and future clinical applications," *Lasers Surg. Med.*, 17:315–349, 1995.

Basu, Marini, Bauman, et al., "Comparative study of biological glues: cryoprecipitate glue, two-component fibrin sealant, and 'French' glue," *Ann. Thorac. Surg.*, 60:1255–1262, 1995.

Baumler, Messman, Abels, et al., *Photosensitization of Human Colonic Cancer Cells with Indocyanine Green In Vitro*, Seventh Congress of the European Society of Pathobiology, Stresa, Italy; O0110, 1997.

Berglin, Gouras, Sheng, et al., "Tolerance of human fetal retinal pigment epithelium xenografts in monkey retina," *Graefes Arch. Clin. Exp. Ophthalmol.*, 235:103–110, 1997.

Bhatt, Newsome, Fenech et al., "Experimental transplantation of human retinal pigment epithelial cells on collagen substrates," *Am. J Opthalmol.*, 117:214–217, 1994.

Biolo, R., Photochem. and Photobiol. 5959:362–365, 1994.

Campochiaro, Jerdon, Glaser, "The extracellular matrix of human retinal pigment epithelial cells in vivo and its synthesis in vitro," *Invest. Ophthalmol Vis Sci.*, 27:1615–1621, 1986.

Chawla, P. S., et al., "Angiogenesis for the treatment of vascular diseases [editorial] [In Process Citation]," Int Angiol, 18:185–192, 1999.

Cheng, H., et al., "Characterization of a fibrin glue-GDNF slow-release preparation," Cell Transplant, 7:53–61, 1998.

CMA Goff, B. A. et al., 70:474–480, 1994.

Coroneo, Beumont, hollows, "Scleral reinforcement in the treatment of pathologic myopia," *Aust. N. Z. J. Ophtholmol.*, 16:317–320, 1988.

Dobson J. and Wilson M. "Sensitization of oral bacteria in biofilms to killing by light from a low-power laser," *Arch Oral Biol* 37(11):883–887, 1992.

Dobson, J. and M. Wilson, Arch. Oral Biol. 37:883–887, 1992.

Donnenfeld, Perry, Nelson, "Cyanoacrylate temporary tarsorrhaphy in the management of corneal epithelial defects," *Ophthalmic Surg.*, 22:591–593, 1991.

Downs, E. C., et al., "Calcium alginate beads as a slow-release system for delivering angiogenic molecules in vivo and in vitro," *J Cell Physiol*, 152:422–429, 1992.

Dubbelman, de Goeij, van Steveninck, "Photodynamic protein cross-linking," *Biochim. Biophys. Acta.*, 647:87–94, 1981.

Eaton, Bass, Libutti, Schubert, Treat, "Suterless cataract incision closure using laser activated tissue glues," *Proc. SPIE*, 1423:52–57, 1991.

el Dirini, Wang, Ogden, Ryan, "Retinal pigment epithelium implantation in the rabbit: technique and morphology," *Graefes Arch. Clin. exp. Ophthalmol.*, 230:292–300, 1992.

Ennker, Ennker, Schoon, Schoon, Rimpler, Hezer, "Formaldehyde-free collagen glue in experimental lung gluing," *Ann. Thorac. Surg.*, 57:1622–1627, 1986.

Enzenauer, Enzenauer, Reddy, Cornell, West, "Treatment of scleromalacia perforans with dura mater grafting," *Ophthalmic Surg.*, 23:829–832, 1992.

Fawcett, Barker, Dunnett, "Dopaminergic neuronal survival and the effects of bFGF in explant, three-dimensional and monolayer cultures of dembryonic rat ventral mescencephalon," *Exp. Brain Res.*, 106:275–282, 1995.

Ferguson and Griffith, "A vision of cell death: insights into immune privilege," *Immunol. Rev.*, 156:167–184, 1997.

Fickweller, Szeimies, Baumler, et al., "Indocyanin green: intracellular uptake and phototherapeutic effects in vitro, *J. Photochem Photobiol.* B., 38:178–183, 1997.

Foitzik, K., et al., "The TGF-beta2 isoform is both a required and sufficient inducer of murine hair follicle morphogenesis," Dev Biol, 212:278–289, 1999.

Forman, Oz, Lontz, Treat, Forman, Kiernan, "Laser-assisted fibrin clot soldering of human menisci," *Clin. Orthop.*, 310:37–41, 1995.

Gabrielian, Oganesian, patel, Verp, Ernest, "Cellular response in rabbit eyes after human fetal RPE transplantation," *Graefes Arch Clin. Exp. Ophthalmol.*, 237:326–335, 1999.

Gailitis, Thompson, Ren, Morris, Waring, "Laser weldign of synthetic epikeratoplasty lenticules to the cornea," *Refract Corneal Sur.*, 6:430–436, 1990.

Gill, Richter-Rusli, Ghosh, Burrows, Rokita, "Nickel-dependent oxidative cross-linking of a protein," *Chem. Res. Toxicol.*, 10:302–309, 1997.

Golubovic and Parunovic, "Cyanoacrylate glue in the treatment of corneal ulcerations," *Fortschr. Ophthalmol.*, 87:378–381, 1990.

Gouras, Huiyun, Yaohua, Teruyo, Efremova, Kjeldbye, "Patch culturing and transfer of human fetal retinal epithelium," *Graefes Arch. Dlin. Exp. Ophthalmol.*, 232:599–607, 1994.

Gouras, Lopez, Brittis, Kjeldbye, "The ultrastructure of transplanted rabbit retinal epithelium," *Graefes Arch Clin. Exp. Ophthalmol.*, 230:468–475, 1992.

Gray, Bishop, Reeves, Laurent, "Alpha and beta chains of fibrinogen stimulate proliferation of human fibroblasts," *J. Cell Sci.*, 104:409–413, 1993.

Hamblin, Miller, Hasan, "The effect of charge on the interaction of site-specific photoimmunoconjugates with human ovarian cancer cells," *Cancer Res.*, 56:5205–5210, 1996.

He, Wang, Ogden, Ryan, "Transplantation of cultured human retinal pigment epithelium into rabbit subretina," *Graefes Arch. Clin. Exp. Opthalmol.*, 231:737–742, 1993.

Ho, Del Priore, Kaplan, "En block transfer of extracellular maxtrix in vitro," *Curr. Eye Res.*, 15:991–997, 1996.

Hoffman, "The three dimensional question: can clincially relevant tumor drug resistance be measured in vitro?" *Cancer Metastasis Rev.*, 13:169–173, 1994.

Hoffman, "To do tissue culture in two or three dimensions? That is the question," *Stem Cells*, 11:105–111, 1993.

J. Khadem et al., Cornia 13(5): 406–140, 1994.

J. Khadem et al., Cornia 13(5): 406–140, 1994.

Jiang, Jorquera, Streilein, "Subretinal space and vitreous cavity as immunologically privileged sites for retinal allografts," Invest. *Ophthalmol Vis. Sci.*, 34:3347–3354, 1993.

Khadem, Truong, Ernest, "Photodynamic biologic tissue glue," *Cornea*, 13:406–410, 1994.

Khadem, Truong, Ernest, "Photodynamic biologic tissue glue,", *Cornea*, 13:406–410, 1994.

Khouri, R. K., et al., "Tissue generation with growth factors," *Surgery*, 114, 374–379, 1993.

Kim, Bassage, Kempski, del Cerro, Park, Aquavella, "Evaluatino of tissue adhesives inclosure of scleral tunnel incisions," *J. Cataract Refract Surg.*, 21:320–325, 1995.

Kirsch, Canning, Zderic, Hensle, Duckett, "Laser soldering technique for suterless urethral surgery, *Tech. Urol.*, 3:108–113, 1997.

Kleinman, Klebe, Martin, "Role of collagenous matrices in the adhesion and growth of cells," *J. Cell Biol.*, 88:473–485, 1998.

Koller and Papoutsakis, "Cell adhesion in animal cell culture; physiological and fluid mechancial implications," *Bioprocessing Technol.*, 20:61–110, 1995.

Kostenich, Zhuravkin, Zhavrid, "Experimental grounds fo usign chlorin e6 in the photodynamic therapy of malignant tumors," *J. Photochem. Photobiol.* B., 22: 211–217, 1994.

Larrosa J M. Et al., "Antiproliferative effect of intravitreal alpha-tocopherol-and alpha-tocopheryl-acid-succinate in a rabbit model of PVR," *Curr Eye Res.*, 16(10) :1030–1035, 1997.

Laustriat, "Molecular mechanisms of photosensitization," *Biochimie* (Paris), 68:771–778, 1986.

Leahey, Gottsch, Stark, "Clinical expereince with N-butylcyanoacrylate (Nexacry) tissue adhesive," *Ophthalmology*, 100:173–180, 1993.

Leong, J., et al., "Muscle protection following motor nerve repair in combination with leukemia inhibitory factor," J Hand Surg [Am], 24:37–45, 1999.

Li and Turner, "Optimal conditions for long-term photoreceptor cell rescue in RCS rats: the necessity for ehalthy RPE transplants," *Exp. Eye Res.*, 52:669–679,1991.

Liversidge, Grabowski, ralston, Benjamin, Forrester, "Rat retinal pigment epithelial cells expres an inducibvle form of nitric oxide synthase and produce nitric oxide in response to inflammatory cytokines and activated T cells," *Immunology,*.83:404–409, 1994.

Liversidge, McKay, Mullen, Forrester, "Retinal pigment epithelial cells modulate lymphocyte function at the blood-retina barrier by autocrine PGE2 and membrane-bound mechanisms," *Cell Immunol.*, 149:315–330, 1993.

Menovsky, Beek, Thomsen, "Laser(-assisted) nerve repair: a review," *Neurosurg. Rev.*, 18:225–235, 1995.

Mered, Albrecht, Hopps, "Cell growth optimization in microcarrier culture," In vitro Cell *Dev. Biol. Anim.*, 16:859–865, 1980.

Mohammad, J. A. et al., "Increased axonal regeneration through a biodegradable amnionic tube nerve conduit: effect of local delivery and incorporation of nerve growth factor/hyaluronic acid media," Ann Plast Surg, 44:59–64, 2000.

Nehra, A., et al., "Transforming growth factor-beta1 (TGF-beta1) is sufficient to induce fibrosis of rabbit corpus cavernosum in vivo," *J. Urol*, 162:910–915, 1999.

Ness, Pedersen, Bjerkvig, Laerum, Lillehaug, "Three-dimensional growth of glial cell lines affects growth factor and growth factor receptor mRNA levels," *Exp. Cell. Res.*, 214:433–436, 1994.

Ochalek and von Kleist, "Study of the resistance of tumor-cell spheroids to penetration and lysis by activated electro cells," *Int. J. Cancer,* 57:399–405, 1994.

Ochsner, "Photophysical and photobiological processes in the photodynamic therapy of tumuours," *J. Photochem. Photobiol. B.,* 39:1–18, 1997.

Okamoto, H. et al., Lasers in Surg. Med. 12:450–485, 1992.

Olive and Durand, "drug and radiation resistance in spherioids: cell contact and kinetics," *Cancer Metastasis Rev.,* 13:121–138, 1994.

Pearce and Thomsen, "Kinetic models of laser-sittue fusion processes," *Biomed. Sci. Instrum.,* 29:355–360, 1993.

Peshwa, Wu, Sharp, Cerra, Hu, "Mechanistics of formation and ultrastructural evaluation of hepatocyte spheroids," *In vitro Cell Dev. Biol. Anim.,* 32:197–203, 1996.

Pierce, G. F., et al., "In vivo incisional wound healing augmented by platelet-derived growth factor and recombinant c-sis gene homodimeric proteins," *J Exp Med,* 167:974–987, 1988.

Poppas, D. P., et al., "Human albumin solder supplemented with TGF-beta 1 accelerates healing following laser welded wound closure," Lasers Surg Med, 19:360–368, 1996.

Prisell, P. T., et al., "Insulin-like growth factor I increases bone formation in old or corticosteroid treated rats," Acta Orthop Scand, 68:586–592, 1997.

Rayan, V. & Hardingham, T. "The recovery of articular cartilage in explant culture from interleukin-1 alpha: effects on proteoglycan synthesis and degradation," Matrix Biol, 14:263–71, 1994.

Rezai, Lai, Farrokh-Siar et al., "A new method of culturing and transferring of iris pigment epithelium," *Invest. Opthalmol Vis. Sci.,* 38:2255–2260, 1997.

Rooke, Poppas, Choma, Cundiff, Schlossberg, "CO2 laser welding versus conventional microsuture repair in patch-graft urethroplasty,", *Urology,* 41:585–589, 1993.

Ruoslahti, Hayman, Pierschbacher, "Extracellular matrices and cell adhesion," *Arteriosclerosis,* 581:594, 1992.

Russell et al., Can J. App. Spectros. 36:103–107, 1991.

Sakamoto, Sakamota, Murphy et al., "Vessel formation by choroidal endothelial cells in vitro is modulated by retinal pigment epithelial cells," *Arch Ophthalmol.,* 113;512–520, 1995.

Sakiyama-Elbert, S. E. & Hubbell, J. A. "Development of fibrin derivatives for controlled release of heparin-binding growth factors," J Controlled Release, 65:389–402, 2000.

Schlossbert and Poppas, "Tissue welding with lasers," *Semin Urol.,* 9:206–209, 1991.

Schmidt-Erfurth, Diddens, Birngruber, Hasan, "Photodynamic targeting of human retinoblastoma cells using covalent low-density lipoprotein conjugates," i Br. J Cancer, 75:54–61, 1997.

Schober, Ulrich, Sander, Durselen, Hessel, "Laser-induced alteration of collagen:
substructure allows microsurgical tissue welding," *Science,* 232:1421–1422, 1986.

Seaton, Sheedlo, Turner, "A primary role for RPE transplants in the inhibition and regression of neovascularization the RCS rat," *Invest. Ophthalmol. Vs. Sci.,* 35:162–169, 1994.

Sellke, F. W., et al., "Angiogenesis induced by acidic fibroblast growth factor as an alternative method of revascularization for chronic myocardial ischemia," Surgery, 120:182–188, 1996.

Sheardown, H., et al., "A semi-solid drug delivery system for epidermal growth factor in corneal epithelial wound healing," Curr Eye Res, 16:183–190, 1997.

Sheedlo, Li, Turner, "Functional and structural characteristics of photoreceptor cells rescued in RPE-cell grafted retinas of RCS dystrophic rats," *Exp. Eye Res.,* 48:841–854, 1989.

Shopora, M. et al., Lasers in Medical Science 10:43–46, 1995.

Siedentop, Harris, Sanchez, "Autologous fibrin tissue adhesive: factors influencing bonding power," *Laryngoscope,* 98:731–733, 1988.

Siegal and Zaidman, "Surgical removal of cyanoacrylate adhesive after accidenal instillation in the anterior chamber," *Ophthalmic Surg.,* 20:179–181, 1989.

Sierra, "Fibrin sealant adhesive systems: a review of their chemistry, material properties and clinical applications," *J. Biomater. Appl.,* 7:309–352, 1993.

Small, Maitland, Heredia, et al., "Investigation of laser tissue welding dynamics via experiment and modeling," *J. Clin. Laser Med. Surg.,* 15:3–7, 1997.

Soukos, Hamblin, Hasan, "The effect of charge on cellular uptake and phototoxicity of polylsine chlorin(e6) conjugates," *Photochem. Photobiol.,* 65:723–729, 1997.

Spector, Boss, Strecker, "A model three-dimensional cutlure system for mammalian dopaminergic precursor cells: application for functional intracerebral transplantation," *Exp. Neurol.,* 124:253–264, 1993.

Spier and Maroudas, "Microcarriers for animal cell biotechnology: an unfulfilled potential," *Biotechniques,* 17:191–212, 1991.

Sporn, Bunce, Francis, "Cell proliferation on fibrin: modulation by fibrinopeptide cleavage," *Blood,* 86:1802–1810, 1995.

Spotnitz, "Fibrin sealant in the United States: clinical use at the University of Virginia," *Thromb Haemost,* 74:482–485, 1995.

Sternberg, Tiedeman, Prensky, "Sutureless scleral buckle for retinal detachment with thin sclera," *Retina,* 8:247–249, 1988.

Tamai, "Retinal pigment epithelial cell transplantation: perspective," *Nippon ganka Gakkai Zasshi,* 100:982–1006, 1996.

Tamura, Koide, Hada, Shiraha, Tsuji, "Gene expression of liver specific proteins in hepatocyte spheroids in primary culture," *Acta med. Okayama,* 49:161–167, 1995.

Tardieu, M., et al, "Derivatized dextrans mimic heparin as stabilizers, potentiators, and protectors of acidic or basic FGF," J Cell Physiol, 150:194–203, 1992.

Tezel and DelPriore, "Reattachment to a substrate prevents apoptosis of human retinal pigment epithelium," *Graefes Arch. Clin. Exp. Ophthalmol.,* 235:41–47, 1997.

U.S. Pat. No. 5,552,452 van der Ham, Kort, Weijma, Jeekel, "Transient protection of incomplete colonic anastomoses with fibrin sealant: an experimental study in the rat," *J. Surg. Res.,* 55:256–260, 1993.

Vejsada, R., et al., "Synergistic but transient rescue effects of BDNF and GDNF on axotomized neonatal motoneurons," Neuroscience, 84:129–139, 1998.

Verweij, Dubbelman, Van Steveninck, "Photodynamic protein cross-linking," Biochim. *Biophys. Acta.,* 647:87–94, 1981.

Wang, J. S. "Basic fibroblast growth factor for stimulation of bone formation in osteoinductive or conductive implants," Acta Orthop Scand Suppl, 269:1–33, 1996.

Weckerle, "Transplantation of retinal components," *Klin Monatsbi Augenheilkd.,* 206:71–77, 1995.

Williamson, Rezai, Farrokh-Siar, et al., "Biodegradable polymer film as a source of adhesion and formation of human fetal retinal pigment epithelium spheroids," *At: Assoc. of Res. in Vision and Opthalmol.,* 39:100 (Abstract 472), 1998.

Wilson, M. et al., Curr. Micro. 25:77–81, 1992.
Wilson, M. et al., Lasers in Medical Sci. 8:69–73, 1993.
Wilson, M. et al., Oral Microbiol. Immunol. 8:182–187, 1993.
Wilson, M., Intl. Dent. J. 44:187–189, 1994.
Wintermantel, Cima, Schloo, Langer, "Angiopolarity of cell carriers: directional angiogenesis in resorbable liver cell transplantation devices," *EXS.*, 61:331–334, 1992.
Wongpichedchai, Weiter, Weber, Dorey, "Comparison of external and internal approaches for transplantation of autologous retinal pigment epithelium," *Invest. Ophthalmol. Vis. Sci.*, 33:3341–3352, 1992.
Wright and Poppas, "Effectr of laser wavelength and protein solder concentratino on acute tissue repair using laser welding: initial results in a canine ureter model," *Tech. Urol.*, 3:176–181, 1997.
Yamamnoto, M., et al,. "Bone regeneration by transforming growth factor betal released from a biodegradable hydrogel [In Process Citation]," J Controlled Release, 64:133–142, 2000.
Yoshimura, Matsumoto, Shimizu, Mandai, Hata, Ishibashi, "Photocoagulated human retinal pigment epithelial cells produce an inhibitor of vascular endothelial cell proliferation," *Invest. Ophthalmol. Vis. Sci.*, 36:1686–1691, 1995.
Zalta and Wieder, "Closure of leaking filtering blebs with cyanoacrylate tissue adhesive," *Br. J. Ophthalmol.*, 75:170–173, 1991.
Zhang and Xu, "Mechanism of photosensitized oxidation of tyrosine by gallium or zinc phthalocyanine in homogeneous and aqueous micellar media," *J. Photochem. Photobiol. B.*, 24:109–116, 1994.
Zhang, Yokoyama, Ohhashi, "Inhibitory effects of fluorescein isothiocyanate photoactivation on lymphatic pump activity," *Microvasc. Res.*, 54:99–107, 1997.

What is claimed is:

1. A method to weld tissue together, comprising the steps of:
   (a) applying to at least one tissue a composition comprising at least one photosensitizer and at least one proteinaceous compound or at least one lipid; and
   (b) irradiating said composition with electromagnetic energy wherein said irradiating promotes adhesion of said tissue to at least a second tissue and wherein;
      (i) the ratio of total proteinaceous molecules in said composition and said at least one photosensitizer is from about 10:1 to about 1:10;
      (ii) the composition is applied at of from about 10 mg said composition per $cm^2$ of said tissue to about 500 mg said composition per $cm^2$ of said tissue; or
      (iii) said composition has a viscosity of about 40 to about 100 poise before said irradiation.

2. The method of claim 1, wherein said photosensitizer is a cationic azine mon-azo dye or derivative thereof.

3. The method of claim 2, wherein said cationic azine mono-azo dye is neutral red.

4. The method of claim 2, wherein said cationic azine mono-azo dye is Janus Green.

5. The method of claim 1, wherein said photosensitizer is a tri-arylmethane-dye or derivative thereof.

6. The method of claim 5, wherein said tri-arylmethane dye is Malachite Green, Brilliant Green, Crystal Violet, basic fuschin, pararosaniline acetate, methyl green or new fuschin.

7. The method of claim 5. wherein said tri-arylmethane dye is Malachite Green.

8. The method of claim 5, wherein said tri-arylmethane dye is a zwitterionic triarylmethane dye.

9. The method of claim 8, wherein said zwitterionic triarylmethane dye is patent blue VF.

10. The method of claim 1, wherein said photosensitizer is a tetrapyrrole or a derivative thereof.

11. The method of claim 10, wherein said tetrapyrrole is a porphyrin, chlorin, bacteriochlorin, phthalocyanine, naphthalocyanine, texaphyrin, verdin, purpurin or pheophorbide.

12. The method of claim 11, wherein said tetrapyrrole is a chlorin.

13. The method of claim 12, wherein said tetrapyrrole is $chlorin_e 6$.

14. The method of claim 1, wherein said photosensitizer is a cationic thiazine dye or derivative thereof.

15. The method of claim 14, wherein said cationic thiazine dye is Azure A, Azure B, Azure C, Brilliant Green, Crystal Violet or Patent Blue VF.

16. The method of claim 1, wherein said composition further comprises at least a second photosensitizer.

17. The method of claim 16, wherein said at least a second photosensitizer is a cationic azine mon-azo dye, a tri-arylmethane dye, a tetrapyrrole, a cationic thiazine dye, xanthine, an anthracenedione, an anthrapyrazole; an aminoanthraquinone, a phenoxazine dye, a phenothiazine derivative, a chalcogenapyrylium dye or derivatives thereof.

18. The method of claim 1, wherein said composition comprises at least one proteinaceous compound.

19. The method of claim 18, wherein said proteinaceous compound comprises at least one peptide, polypeptide or protein.

20. The method of claim 19, wherein said proteinaceous compound comprises at least one protein.

21. The method of claim 20, wherein said protein is albumin, fibrinogen or gelatin.

22. The method of claim 21, wherein said protein is albumin.

23. The method of claim 1, wherein said composition is a non-covalent mixture.

24. The method of claim 1, wherein at least one covalent bond conjugates said photosensitizer to said proteinaceous composition or said lipid.

25. The method of claim 24, wherein said covalent bond is part of a linking moeity.

26. The method of claim 24, wherein said composition comprises at least a second proteinaceous compound not covalently conjugated to said photosensitizer.

27. The method of claim 26, wherein the proteinaceous compound covalently conjugated to said photosensitizer is the same type as the proteinaceous compound not covalently conjugated to said photosensitizer.

28. The method of claim 1, wherein the ratio of total proteinaceous molecules in said composition and said at least one photosensitizer is from about 10:1 to about 1:10.

29. The method of claim 28, wherein the ratio of total proteinaceous molecules in said composition and said at least one photosensitizer is from about 3:1 to about 1:1.

30. The method of claim 29, wherein the ratio of total proteinaceous molecules in said composition and said at least one photosensitizer is about 2:1.

31. The method of claim 1, wherein said composition comprises at least one lipid.

32. The method of claim 31, wherein said lipid further comprises at least one proteinaceous compound.

33. The method of claim 32, wherein said proteinaceous compound is a lipoprotein.

34. The method of claim 1, wherein said composition further comprises at least one therapeutic agent.

35. The method of claim 34, wherein said agent is a chemical, a drug, a proteinaceous molecule, a nucleic acid, a lipid, an antibody, an antigen, a hormone, a nutritional substance, a cell or a combination thereof.

36. The method of claim 35, wherein said agent is a hormone.

37. The method of claim 36, wherein said hormone is a growth factor.

38. The method of claim 37, wherein said growth factor is transforming growth factor beta, basic fibroblast growth factor, epidermal growth factor, vascular endothelial growth factor, nerve growth factor, acidic fibroblast growth factor, insulin like growth factor, heparin binding growth factor, brain-derived neurotrophic factor, glial cell line-derived neurotrophic factor, platelet-derived growth factor, leukemia inhibitory factor or combination thereof.

39. The method of claim 35, wherein said agent is a cell.

40. The method of claim 39, wherein said cell is an embryonic cell.

41. The method of claim 1, wherein said tissue is skin, bone, neuron, axon, cartilage, blood vessel or cornea.

42. The method of claim 1, wherein said second tissue is the same tissue type as said at least a first tissue.

43. The method of claim 1, wherein said second tissue is a different tissue type as said at least one tissue.

44. The method of claim 1, wherein said composition has a viscosity of about 40 to about 100 poise before said irradiation.

45. The method of claim 1, wherein said composition is applied at of from about 10 mg said composition per $cm^2$ of said tissue to about 500 mg said composition per $cm^2$ of said tissue.

46. The method of claim 45, wherein said composition is applied of from about 20 mg said composition per $cm^2$ of said tissue to about 100 mg said composition per $cm^2$ of said tissue.

* * * * *